(12) United States Patent
Fischer, Jr. et al.

(10) Patent No.: US 11,013,888 B2
(45) Date of Patent: May 25, 2021

(54) CATHETERS AND SYSTEMS USEFUL FOR DELIVERY OF MATERIAL TO THE LUNG

(71) Applicant: Cook Regentec LLC, Indianapolis, IN (US)

(72) Inventors: Frank J. Fischer, Jr., Bloomington, IN (US); Michael P. DeBruyne, Bloomington, IN (US)

(73) Assignee: Cook Regentec LLC, Indianapolis, IN (US)

( * ) Notice: Subject to any disclaimer, the term of this patent is extended or adjusted under 35 U.S.C. 154(b) by 971 days.

(21) Appl. No.: 15/208,809

(22) Filed: Jul. 13, 2016

(65) Prior Publication Data

US 2017/0189644 A1    Jul. 6, 2017

Related U.S. Application Data

(60) Provisional application No. 62/192,006, filed on Jul. 13, 2015.

(51) Int. Cl.
    *A61M 25/00*      (2006.01)
    *A61M 11/00*      (2006.01)
    (Continued)

(52) U.S. Cl.
    CPC ......... *A61M 25/0026* (2013.01); *A61B 1/018* (2013.01); *A61B 1/2676* (2013.01);
    (Continued)

(58) Field of Classification Search
    CPC .......... A61M 25/0026; A61M 25/0102; A61M 2025/0073; A61M 16/04; A61M 16/0427;
    (Continued)

(56) References Cited

U.S. PATENT DOCUMENTS 5,199,950 A    4/1993    Schmitt et al.
5,254,088 A    10/1993    Lundquist et al.
(Continued)

FOREIGN PATENT DOCUMENTS

EP    0 489 937 A1    6/1992
EP    0 692 273 A1    1/1996

OTHER PUBLICATIONS

International Application No. PCT/US2016/042066 Written Opinion, dated Jan. 16, 2018.
(Continued)

*Primary Examiner* — Jan Christopher L Merene
*Assistant Examiner* — Cana A Gallegos
(74) *Attorney, Agent, or Firm* — Woodard, Emhardt, Henry, Reeves & Wagner, LLP

(57) ABSTRACT

A device for introducing material into a body cavity is shown. The device includes a catheter with a distal tip. A first lumen extends through the catheter. The catheter is configured to faun a mist from liquid passed through the first lumen, for example including a misting nozzle in fluid communication with the first lumen and configured to provide a mist from a flow of liquid through the first lumen. An inflatable balloon may be included on the catheter to allow the user to isolate the portion of the body in which the material is introduced. Additional described features can provide for controlled deflection of a distal region of the catheter, guidewire or guide loop tool lumens, misting nozzles on the catheter, and delivery apparatuses including the catheter devices coupled to endoscopes such as bronchoscopes. Methods of use of the catheter devices and delivery apparatuses are also described.

18 Claims, 18 Drawing Sheets

(51) Int. Cl.
*A61B 1/267* (2006.01)
*A61B 1/018* (2006.01)
*A61M 25/10* (2013.01)
*A61M 31/00* (2006.01)
*A61M 25/01* (2006.01)

(52) U.S. Cl.
CPC ........ *A61M 11/00* (2013.01); *A61M 25/0068* (2013.01); *A61M 25/10* (2013.01); *A61M 31/00* (2013.01); *A61M 25/0102* (2013.01); *A61M 25/0136* (2013.01); *A61M 25/0147* (2013.01); *A61M 2025/0073* (2013.01); *A61M 2025/1052* (2013.01); *A61M 2210/1032* (2013.01); *A61M 2210/1035* (2013.01); *A61M 2210/1039* (2013.01)

(58) Field of Classification Search
CPC .......... A61M 25/0133; A61M 25/0147; A61M 25/10; A61M 2025/105; A61M 25/0136; A61M 25/015; A61M 2025/0186; A61B 1/018; A61B 2017/22045; A61B 1/00091; A61B 1/00119; A61B 1/00128; A61B 1/012; A61B 1/015
See application file for complete search history.

(56) References Cited

U.S. PATENT DOCUMENTS

| | | | |
|---|---|---|---|
| 5,443,447 A | 8/1995 | Kassis | |
| 6,112,743 A | 9/2000 | Denton | |
| 6,146,355 A * | 11/2000 | Biggs | A61M 25/0136 604/95.01 |
| 6,227,195 B1 | 5/2001 | Gonda | |
| 6,951,555 B1 * | 10/2005 | Suresh | A61M 25/0023 604/524 |
| 7,341,208 B2 | 3/2008 | Peters et al. | |
| 2003/0172934 A1* | 9/2003 | Croll et al. | A61M 16/0486 128/207.14 |
| 2005/0070844 A1* | 3/2005 | Chow et al. | A61M 25/0054 604/95.04 |
| 2009/0107503 A1* | 4/2009 | Baran | A61M 16/0486 128/204.25 |
| 2009/0199848 A1* | 8/2009 | Sharratt | A61M 31/00 128/200.14 |
| 2011/0245665 A1* | 10/2011 | Nentwick | A61M 25/0029 600/433 |
| 2013/0211320 A1* | 8/2013 | Alkhamesi | A61M 13/003 604/24 |
| 2015/0217084 A1* | 8/2015 | Tassoni, Jr. | A61L 29/04 29/428 |

OTHER PUBLICATIONS

International Application No. PCT/US2016/042066 International Search Report and Written Opinion, dated Jan. 12, 2017.
European Search Report issued in Application No. 20155474.8-1132 dated Aug. 27, 2020, 13 pgs.

* cited by examiner

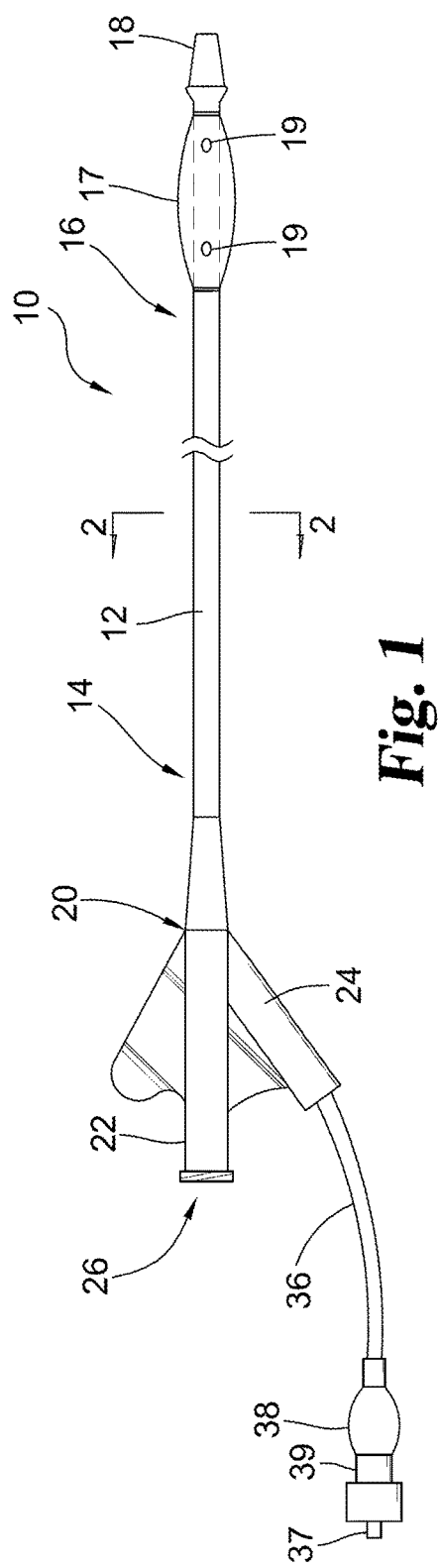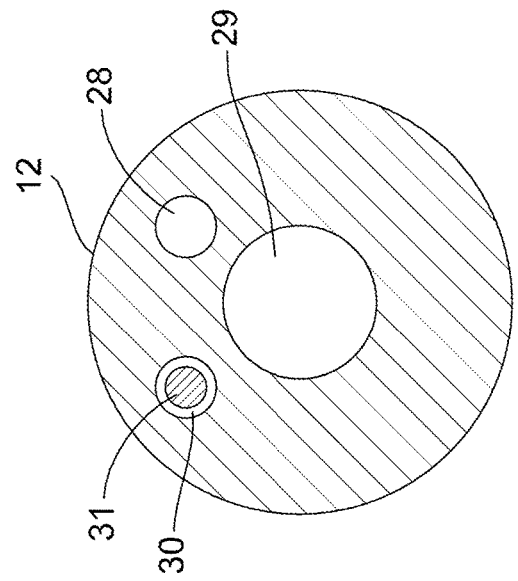

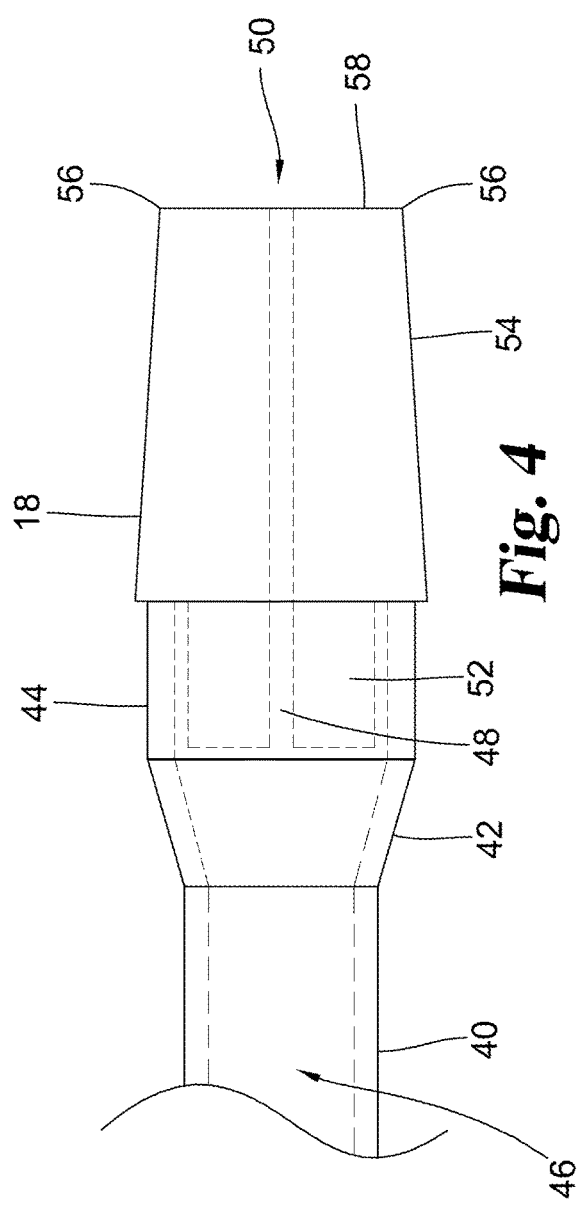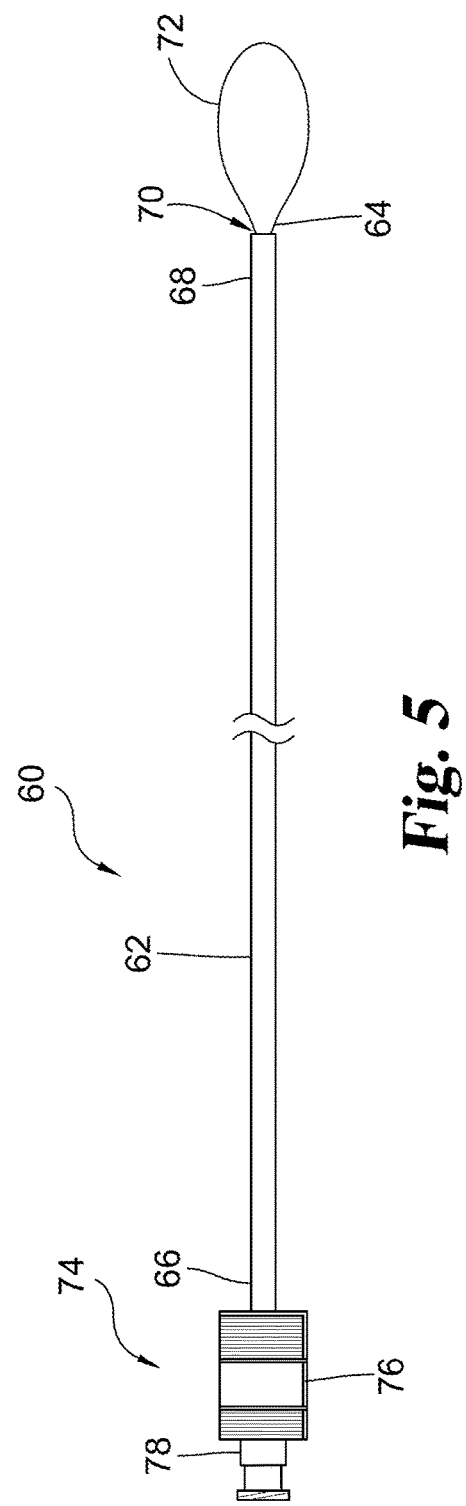

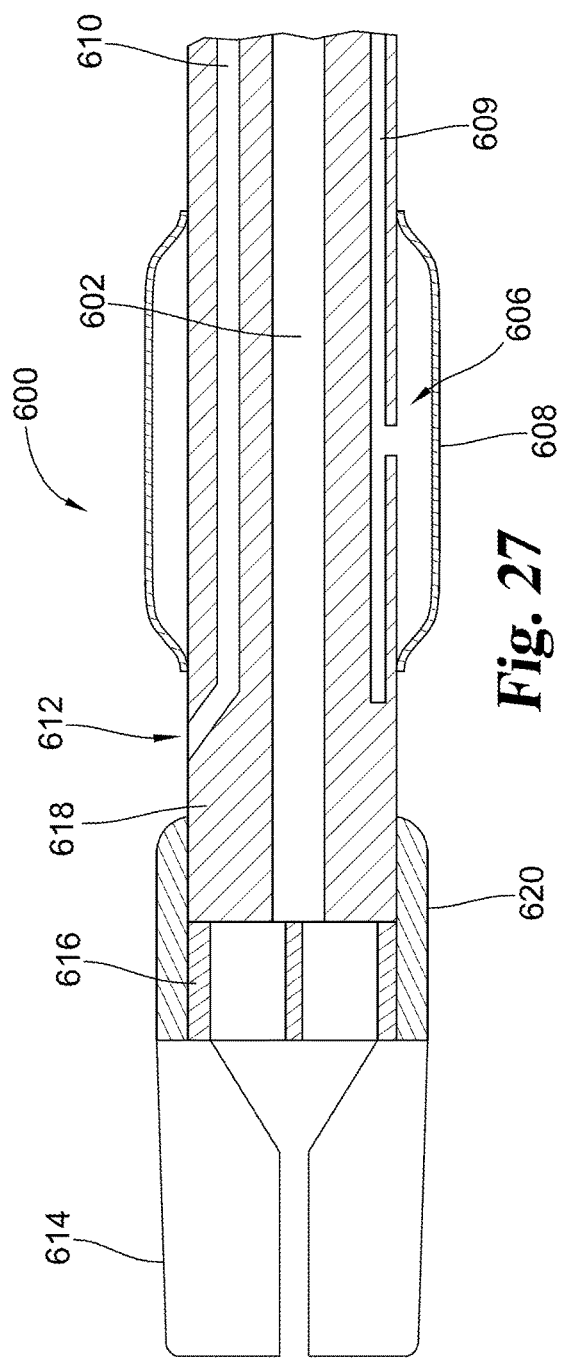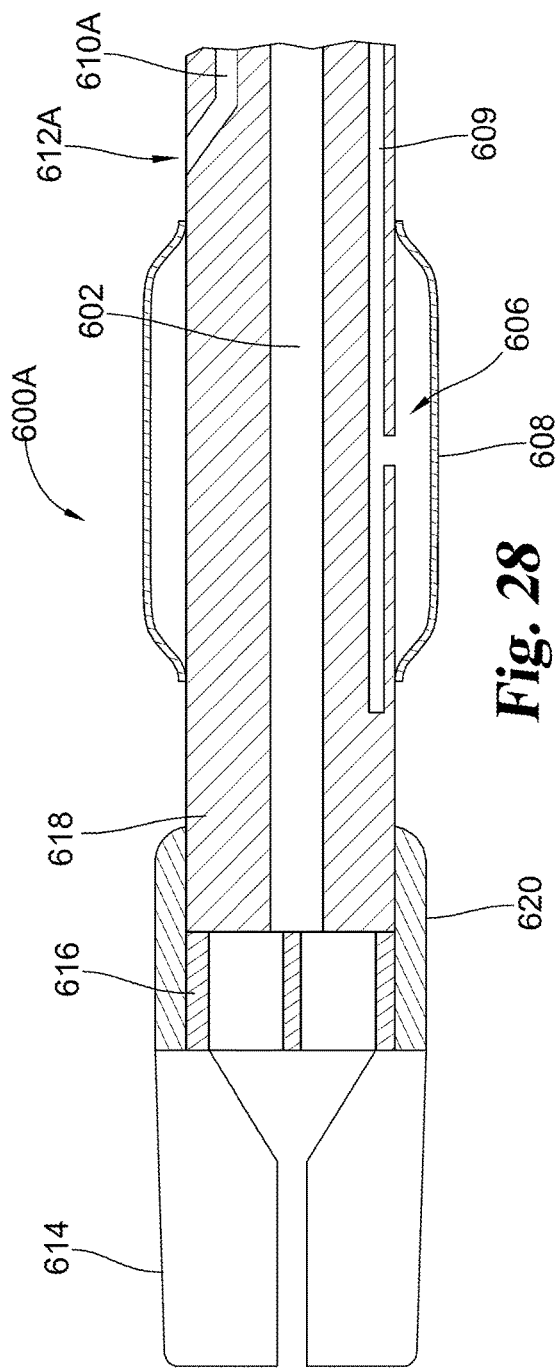

CATHETERS AND SYSTEMS USEFUL FOR DELIVERY OF MATERIAL TO THE LUNG

REFERENCE TO RELATED APPLICATION

This application claims the benefit of priority of U.S. Provisional Patent Application Ser. No. 61/192,006 filed Jul. 13, 2015, which is hereby incorporated herein by reference in its entirety.

BACKGROUND

The present disclosure pertains generally to devices for the introduction of materials into a bodily passage of a patient. More particularly but not exclusively, embodiments of the present disclosure are useful as catheters or systems for delivery of biologics and therapeutic agents directly into the tracheobronchial tree.

Chronic Obstructive Pulmonary Disease (COPD) is a disease characterized by persistent airflow limitation of a patient's airways and lungs. Symptoms can include dyspnea, chronic cough, and chronic sputum production. COPD can have a significant impact on the health of a patient as it may coexist with other diseases and cause serious long-term disability or death.

There is currently no cure to COPD, however, approved treatments include inhaled bronchodilators, inhaled corticosteroids, and a combination of inhaled corticosteroid/bronchodilator therapy.

Recent results from animal research and clinical trials indicate that COPD may potentially be treated with stem cell therapy. These trials have included intravenous injection of stem cells and inhalation of nebulized stem cells. Intravenous injection relies on cells moving through the venous system before engrafting into lung tissue. However, using this method, cells may be lost as they contact venous system surfaces and engraft to them, causing only a percentage of the stem cells injected to be delivered to lung tissue. Nebulizer inhalation of stem cells relies on cells moving from the nebulizer chamber through the oral or nasal cavity and trachea before engrafting onto lung tissue. Problems also arise with this method, as not all of the stem cells are able to be nebulized, and cells are lost as they contact the nasal, oral, and trachea passageway surfaces and engraft to the tissue. Stem cells may also be lost as they are exhaled during the patient's normal breathing process. Additionally, droplet size may limit the number of cells that are actually delivered to the lung, as larger stem cells are deposited in the mouth and the throat. As a result, only a percentage of the stem cells introduced using nebulizer inhalation are actually delivered to the lung tissue.

In view of this background, needs remain for improved or alternative methods of and devices or systems for the introduction of biologic agents or therapeutic agents into patient passageways, such as airways.

SUMMARY

In certain aspects, the present invention provides a device for introducing a material into a body cavity. Further forms, objects, features, aspects, benefits, advantages, and embodiments of the present invention will become apparent from a detailed description and drawings provided herewith.

Accordingly, in one embodiment, the present disclosure provides a catheter device for introducing a material into a body cavity. The device includes a catheter shaft having a proximal portion and a distal portion. A first lumen extends through the catheter shaft from the proximal portion to the distal portion. The catheter device is configured to form a mist from a liquid passed through the first lumen from the proximal portion to the distal portion. Preferably, a misting nozzle is carried on the distal portion and is in fluid communication with the first lumen, with the misting nozzle being configured to receive a flow of liquid through the first lumen and form a mist of the liquid. A second lumen also extends through the catheter shaft from the proximal portion to the distal portion. A deflecting wire is received in the second lumen, the deflecting wire having a first portion attached to the distal portion of the catheter shaft and a second portion positioned in the proximal portion of the catheter shaft. An actuator is coupled to the second portion of the deflecting wire and selectively operable to tension the deflecting wire to deflect the distal portion of the catheter shaft. In certain embodiment, deflection of the distal portion of the catheter shaft can be used to facilitate steering the catheter. Additionally or alternatively, in certain embodiments, deflection of the distal portion of the catheter shaft can be used to control a throw direction of a mist formed by the catheter device, e.g. a mist ejected from the misting nozzle.

In another embodiment, a catheter device for introducing a material into a body cavity includes a catheter shaft and a first lumen extending through the catheter shaft. A misting nozzle is in fluid communication with the first lumen and is configured to provide a mist from a flow of liquid through the first lumen. The misting nozzle defines an outer profile within a longitudinal profile of the catheter device. A second lumen extends through the catheter, the second lumen having a distal end opening defining an outer profile within the longitudinal profile of the catheter device. The outer profile defined by the misting nozzle does not overlap the outer profile defined by the distal end opening of the second lumen.

In some preferred embodiments, the catheter devices herein have an inflatable balloon that is positioned proximal of the distal tip of the catheter. The catheter devices may include a third lumen that allows passage of air or another fluid for inflating the balloon. In addition or alternatively, in other preferred embodiments, the catheter devices are combined with a guide wire or guide loop device that is slidably insertable into the second lumen. When used, a loop portion of the guide loop device extends distally from the distal tip of the catheters.

In another embodiment, provided is a catheter device including a distal tip and a first lumen that extends through the catheter and has a distal end. The catheter also includes a second lumen that contains a tip deflecting wire. Tensioning of the tip deflecting wire deflects the distal tip of the catheter, and release or reduction of the tension causes the tip to return toward or to its position prior to the application of tension. The catheter device is configured to form a mist from a liquid passed through the first lumen toward the distal end of the first lumen. Preferably, the catheter device includes a misting nozzle in fluid communication with the first lumen and configured to provide a mist from a flow of liquid. The catheter may also include an inflatable balloon proximal of the distal tip of the catheter and a third lumen that allows passage of air for inflating the inflatable balloon. Additionally or alternatively, the catheter can include an actuator housing that houses an actuator attached to the deflecting wire. In some embodiments an injection port of the catheter device can fluidly communicate with an interior of the actuator housing such that flowable material passed into the injection port enters the actuator housing and contacts one or more components of the actuator and/or the deflecting wire prior to passing into the first lumen of the catheter device. In other embodiments an injection port of the catheter device does not communicate with the interior of such an actuator housing of the catheter device, but rather provides a separate and independent path for the flowable material to enter the first lumen of the catheter for generation of a mist from the flowable material, and in preferred embodiments for passage to and through the misting nozzle to form the mist.

In another embodiment, provided is an assembly for accessing a body cavity. The assembly includes a catheter device having a catheter shaft. The catheter shaft includes a distal tip and a first lumen extending through the catheter shaft and defining a first lumen distal end. Optionally, the catheter device is configured to form a mist from a liquid passed through the first lumen toward the first lumen distal end, with preferred embodiments having a misting nozzle fluidly coupled to the first lumen and configured to provide a mist from a flow of liquid through the first lumen. The assembly further includes an endoscope, such as a bronchoscope, having an endoscope shaft. The endoscope shaft has an endoscope lumen extending therethrough and defining an endoscope lumen distal end opening. The assembly also includes a guide loop device received through the endoscope lumen. The guide loop device has a distal end loop, with the distal end loop external of and distal of the endoscope lumen distal end opening. The distal end loop of the guide loop device or tool is slidably received around the catheter shaft.

In another embodiment, provided is an assembly for accessing a body cavity. The assembly includes a catheter having a catheter shaft. The catheter shaft includes a distal tip and a first lumen extending through the catheter shaft and defining a first lumen distal end. The catheter device is configured to form a mist from a liquid passed through the first lumen toward the first lumen distal end, with preferred embodiments having a misting nozzle fluidly coupled to the first lumen and configured to provide a mist from a flow of liquid through the first lumen. A second lumen extends through the catheter and has a distal end opening. The assembly also includes a guide loop device having a distal end loop received through the second lumen, with the distal end loop external of and distal of the distal end opening of the second lumen. The assembly further includes an endoscope, such as a bronchoscope, having an endoscope shaft. The distal end loop of the guide loop device is slidably received around the endoscope shaft.

Another embodiment provides a method of introducing a flowable material, such as a biologic or therapeutic material, into the airway passages of a patient. The method includes inserting a catheter into the airway passages of a patient and positioning the catheter adjacent to the portion of the airway passages on which the material is to be introduced. The material is passed through a first lumen of the catheter and converted to a mist that is directed onto a portion of the airway passages. In preferred embodiments, the material passes through a misting nozzle in fluid communication with the first lumen. When it passes through the misting nozzle, the material is converted to a mist that is directed onto a portion of the airway passages. The catheter may also include an inflatable balloon that can be inflated to isolate the portion of the airway passages to which the material is to be applied.

Another embodiment provides a catheter device for introducing a material into a body cavity. The device includes a catheter shaft having a proximal portion and a distal portion, a first lumen extending through the catheter shaft from the proximal portion to the distal portion, and a second lumen extending through the catheter shaft from the proximal portion to the distal portion. The device further includes a first misting nozzle carried on the distal portion and fluidly coupled to the first lumen, the misting nozzle configured receive a flow of liquid through the first lumen and form a mist of the liquid, and a second misting nozzle carried on the distal portion and fluidly coupled to the second lumen, the misting nozzle configured receive a flow of liquid through the first lumen and form a mist of the liquid. In some forms, the first and second misting nozzles can be of the same construction. In other forms, the first misting nozzle and the second misting nozzle can be of different construction. In still other embodiments, the first misting nozzle can have a first spray pattern and the second misting nozzle has a second spray pattern that at least partially overlaps the first spray pattern, and in preferred forms of such embodiments the positions of the first and second misting nozzles can be fixed relative to one another to maintain a consistent overlap of their respective spray patterns during use of the catheter device.

Another embodiment provides a method for introducing a material into a body passageway. The method includes introducing a distal portion of a catheter shaft into a region of a body passageway of a patient, the catheter shaft also having a proximal portion, a first lumen extending through the catheter shaft from the proximal portion to the distal portion, a second lumen extending through the catheter shaft from the proximal portion to the distal portion, a first misting nozzle carried on the distal portion and fluidly coupled to the first lumen, the misting nozzle configured receive a flow of liquid through the first lumen and form a mist of the liquid, and a second misting nozzle carried on the distal portion and fluidly coupled to the second lumen, the misting nozzle configured receive a flow of liquid through the first lumen and form a mist of the liquid. The method further includes first delivering a first flowable liquid medium through the first lumen and the first misting nozzle to create a mist of the first flowable liquid medium, and second delivering a second flowable liquid medium through the second lumen and the second misting nozzle to create a mist of the second flowable liquid medium.

It will be understood that the device and method embodiments disclosed in this Summary above can include additional individual features, or combinations of features, as disclosed in connection with the embodiments in the Detailed Description below.

Additional embodiments, as well as featured and advantages of embodiments of the invention will be apparent from the descriptions herein.

BRIEF DESCRIPTION OF THE DRAWINGS

FIG. 1 provides a perspective view of a catheter device.

FIG. 2 provides a cross-sectional view taken along line 2-2 of FIG. 1 and viewed in the direction of the arrows.

FIG. 4 provides an enlarged view of a distal tip of the catheter device of FIG. 1.

FIG. 5 provides a perspective view of a loop guide wire tool usable in conjunction with catheter assemblies.

FIG. 27 provides an enlarged cross-sectional view of a distal region of another catheter device.

FIG. 28 provides an enlarged cross-sectional view of a distal region of another catheter device.

DETAILED DESCRIPTION

Figure 3:
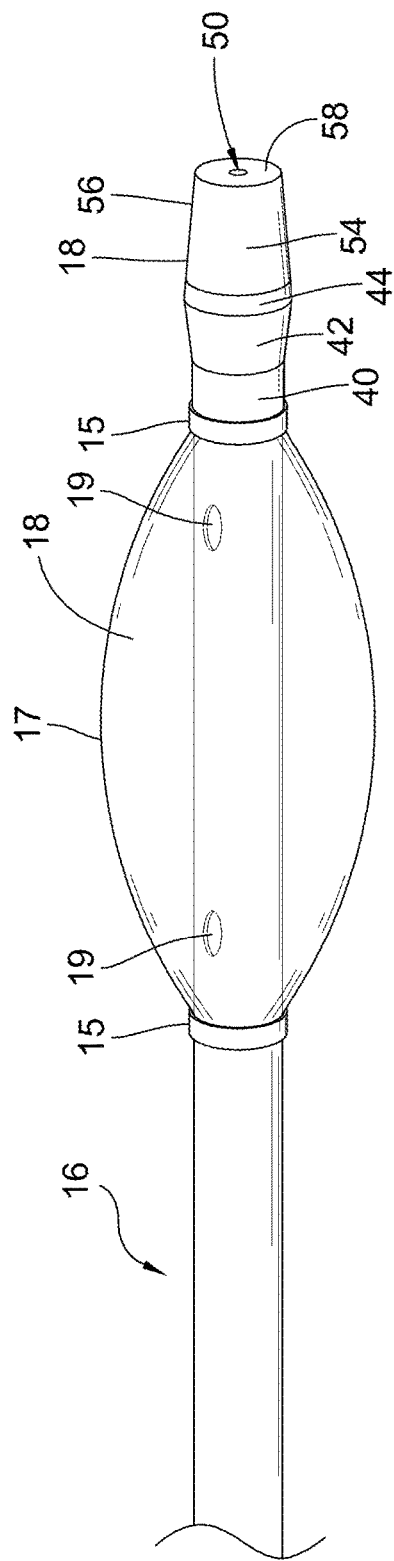
FIG. 3 provides an enlarged view of a distal region of the catheter device of FIG. 1.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

In certain aspects, the invention can include a catheter device for introducing a material into a body cavity. The catheter includes a catheter shaft that has a proximal and distal end. The proximal end is attached to a proximal hub. The proximal hub may be branched and have openings for attachment to an injection port, an inflation port, and/or a wire guide port.

A variety of lumens may run through the catheter extending from the proximal end of the catheter shaft to points at or near the distal end of the catheter shaft. The catheter can include an injection lumen that is large enough to allow passage of a flowable material or a liquid. The catheter may also have a guide lumen that is sized to allow a guide wire or a guide loop device to be inserted inside the guide lumen. In place of a guide lumen, the catheter may have a tip deflecting wire lumen that is sized to house a tip deflecting wire. The catheter may also have a balloon inflation lumen that is in fluid communication with an inflatable balloon positioned around the catheter shaft.

The catheter shaft also has a distal end that ends at a distal tip. The inflatable balloon can be located proximate to the distal end, but is proximal of the distal tip. The balloon inflation lumen may extend through the catheter device, creating an opening at the distal tip of the catheter shaft. If the catheter has a guide lumen, the guide lumen may also extend through the catheter device, creating a distal lumen opening, in some forms at the distal end of the catheter shaft. If, instead, the catheter has a tip deflecting wire lumen, the tip deflecting wire lumen may terminate before the end of the catheter shaft. The balloon inflation lumen may also terminate before the end of the catheter shaft.

The catheter device can be configured to form a mist from a liquid or other flowable material passed through the injection lumen. In some embodiments, the catheter device includes a misting nozzle in fluid communication with the injection lumen, e.g. with the misting nozzle positioned at or proximate to the distal tip of the catheter. The distal end of the misting nozzle can extend distally past the distal tip of the catheter shaft. The misting nozzle may provide a mist from liquid injected into the injection lumen and spray the mist on a location where treatment is desired. The misting nozzle may be a standard misting or atomizer nozzle design, such as, but not limited to, designs like a plain-orifice, simplex, dual-orifice or spinning disc. Nozzle designs may allow for different spray patterns of material such as fine, flat fan, hollow cone, wide cone, and full cone. Many misting nozzles are commercially available and can be used in embodiments herein. In certain embodiments, the misting nozzle can have a whirl or swirl nozzle construction, for example as available in the LMA MAD Nasal intranasal mucosal atomization device sold commercially by Teleflex Medical, Research Triangle Park, N.C., USA. In additional embodiments, other mechanisms or adaptations for generating a mist from the liquid can be provided by the catheter. Illustratively, in addition to the injection lumen, the catheter may include other lumen(s) adjacent to or surrounding the injection lumen (e.g. an annular lumen surrounding the injection lumen), through which a gas can be passed while the liquid is passed through the injection lumen, with the gas and the liquid interacting after they exit from their respective lumens to form a mist. These and other mist generation configurations for the catheter device will be within the purview of those of ordinary skill from the descriptions herein.

In some embodiments herein, when the catheter device is viewed from the end in a longitudinal direction, a provided misting nozzle has an outer profile and a guide wire lumen opening at the distal tip of the catheter shaft has an outer profile, and the outer profile of the misting nozzle does not overlap the outer profile of the guide wire lumen opening. In this manner, a guide wire can be passed through the guide wire lumen and out the guide wire lumen opening, and not contact the misting nozzle. This allows a smoother passage of the catheter along the guide wire.

In various aspects herein, the number of lumens located within the catheter device may vary to include different combinations of lumens. For example, the catheter device may be a triple lumen catheter having an injection lumen, a balloon inflation lumen, and a guide wire lumen or a tip deflecting wire lumen. In certain embodiments, the triple lumen catheter has a misting nozzle in fluid communication with the injection lumen. In other embodiments, the triple lumen catheter does not have a misting nozzle in fluid communication with the injection lumen.

The catheter device may also be a double lumen catheter. For example, the catheter may include only an injection lumen and a guide wire lumen, or the catheter may include only an injection lumen and a tip deflecting wire lumen. In another example, the catheter device may include an inflatable balloon, and may include an injection lumen and a balloon inflation lumen.

The double lumen catheter may include a misting nozzle in fluid communication with the injection lumen. In still other embodiments, the catheter device may also contain only a single lumen, and may have a misting nozzle in fluid communication with the single lumen. As discussed further herein, single lumen, double lumen, triple lumen or other catheters herein may be used as components of delivery assemblies, in combination with other devices such as endoscopes, wire guides, and/or guide loop devices.

The catheter shaft may be constructed from any standard catheter material such as, but not limited to, nylon or polyurethane. The inflatable balloon may be made from a compliant, semi-compliant or non-compliant material, and in certain embodiments comprises silicone or polyurethane. The inflatable balloon may have a durometer such that, as the inflatable balloon is inflated and expands in diameter beyond its manufactured diameter, it will maintain its general shape.

A pressure gauge may be connected between the injection port of a catheter device as described herein and a syringe or other reservoir that contains a flowable material, e.g. any flowable material described herein, to be passed under pressure into the injection lumen of the catheter device. The pressure gauge monitors the injection pressure and may include a male luer lock on one end to connect to the injection port and a female luer lock on the other end to connect to the syringe or other reservoir.

With reference now to the various figures, FIG. 1 depicts a side elevational view of one embodiment of a catheter 10 of the present invention, useful for example as an endobronchial blocker catheter. In the following discussion, the terms "proximal" and "distal" will be used to describe the opposing axial ends of the apparatus, as well as the axial ends of various component features. The "proximal" end refers to the end of the catheter (or component thereof) that is closest to the operator during use of the assembly. The "distal" end refers to the end of the catheter (or component) that is initially inserted into the patient, or that is closest to the patient. In the orientation of catheter 10 and each of its component features shown in the figures herein, the proximal end is to the left of the page, while the distal end is to the right.

As shown in FIG. 1, catheter 10 includes an elongated catheter shaft 12 having a proximal end 14 and a distal end 16. An inflatable blocker balloon 17 is disposed about a portion of the distal region of the catheter shaft 12. Catheter shaft 12 is preferably formed from a conventional pliable polymeric material such as polyurethane, fluoroplastic, polyester, nylon, polypropylene or a silicone. A hub 20 is attached at proximal end 14. Hub 20 includes two extended portions 22, 24. Extended portion 24 is connected to one end of an inflation tube 36. A conventional inflation assembly, such as pilot balloon 38 and one-way valve 39, is provided at the other end of inflation tube 36 for receiving an inflation fluid through end 37 for use in inflating blocker balloon 17. Extended portion 22 is fitted with a connector for making a fluid-tight connection, such as an external threaded connector. A spray nozzle 18 is connected to the distal end of catheter shaft 12.

FIG. 2 illustrates an enlarged cross-sectional view of catheter 10 of FIG. 1 taken along line 2-2 and viewed in the direction of the arrows. In this embodiment, catheter shaft 12 includes three lumens 28, 29, 30 therein. Lumen 28, comprising the balloon inflation lumen, extends substantially through catheter shaft 12. Lumen 28 is closed off at the distal end of body 12 (e.g. by filling the closed portion with a material such as an adhesive or polymer), causing lumen 28 to communicate only with interior 18 of balloon 17 through ports 19. As stated, the proximal end of lumen 28 communicates with inflation tube 36 and inflation assembly 38, 39. Lumen 29, which is larger than lumens 28 and 30, fluidly communicates with the input of misting nozzle 18 and with opening 26 of extended portion 22 of hub 20. Lumen 30 has received and fixed therein a stiffening member 31, such as a stiffening mandrel, to increase the stiffness of catheter shaft 12. Stiffening member 31 extends substantially the length of catheter shaft 12. Other features of the inventive catheter 10 are similar in many respects to corresponding features in U.S. Pat. No. 5,904,648, which is incorporated herein by reference.

FIG. 3 illustrates an enlarged, pictorial view of distal portion 16 of catheter 10 of FIG. 1, showing inflatable blocker balloon 17 in an inflated state. Balloon 17 can be made from a conventional elastomeric material, such as a silicone rubber material. Other conventional balloon compositions, for example latex rubber, polyurethane or silicone polymeric materials, may be used as well. The leading and trailing ends of balloon 17 are attached to elongated blocker body 12 at balloon attachment regions 15 using, for example, a conventional medical grade adhesive. The balloon shown in FIG. 3 forms a generally elliptical shape when interior 18 of the balloon is inflated. During inflation, an inflation fluid from inflation assembly 38, 39 passes through balloon inflation lumen 28 and communicates with the interior of balloon 17 through one or more exit ports 19 disposed in catheter body 12 and opening into the interior of balloon 17. Those skilled in the art will appreciate that other conventional balloon shapes, such as a spherical shape, a cylindrical shape, and the like, may be used in place of the elliptical shape illustrated in FIG. 3.

With continued reference to FIG. 3 along with FIG. 4, in the illustrated embodiment, catheter shaft has a region 40 distal of the balloon 17 that is of equal outer diameter to the remainder of shaft 12, connected to a region 42 distal thereof that has outwardly (enlarging) tapered outer and inner diameters, in turn connected to a region 44 distal thereof of a constant outer and inner diameters. Regions 40, 42 and 44 can, for example, be provided by a molded or formed tubular segment that is bonded to the distal end of triple lumen catheter shaft 12, with the tubular segment defining an inner lumen 46 for receiving flow from lumen 29 and transmitting the flow to the input lumen 48 of misting nozzle 18. Misting nozzle 18 has an exit opening 50 from which a mist of liquid formed by nozzle 18 is thrown, e.g. in a throw direction generally distal of opening 50. For connection to region 44, misting nozzle 18 has a stem portion 52 received within lumen 46 and sealed fluid-tight to the tube walls defining lumen 46, for example with a conventional adhesive. In one preferred embodiment, misting nozzle has a leading end that includes a longitudinally-extending cylindrical outer wall 54 transitioning through a radiused corner 56 to a generally flat leading face 58. Radiused corner 56 can be beneficial in reducing or preventing the incidence of catching or "hanging up" of misting nozzle 18 on tissue of the patient during advancement of catheter 10 within passageways of the patient.

Figure 3A:
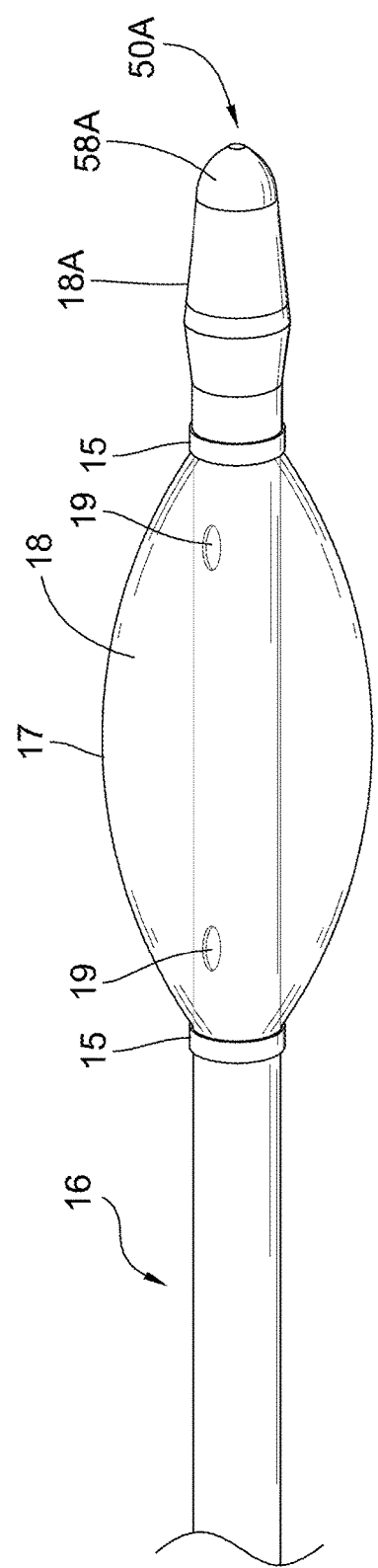
FIG. 3A provides an enlarged view of an alternative distal region for a catheter device of FIG. 1.

Referring now to FIG. 3A, shown is another preferred embodiment of catheter 10 in which misting nozzle 18A has a rounded leading face 58 that defines a generally continuous convex curve, for example defining a segment of a sphere (e.g. a hemispherical leading face), a segment of an ellipsoid, or a paraboloid. Such rounded leading faces can be used to provide a bullet nose to the misting nozzle 18A, which also provides a beneficial character in reducing or preventing the incidence of catching of misting nozzle 18 on tissue during advancement of catheter 10 within passageways of the patient. Nozzle exit opening 50A can be located on face 58A, for example generally centrally located thereon. Misting nozzle 18A can be similar to misting nozzle 18 in other aspects of its construction and integration into catheter 10.

FIG. 5 depicts a side view of a guide loop device 60 that can be used in conjunction with an endoscope to guide catheter 10 (FIGS. 1-4) through a body passageway such as a passageway within a lung. Guide loop device 60 has a tube 62 preferably formed from a flexible polymer such as a polyaryletherketone. Although tube 62 may be generally flexible, it should have at least sufficient stiffness to enable it be passed through a working lumen of an endoscope or similar device without significant buckling or kinking. A filament such as a wire 64, folded over on itself, extends in the distal direction from the proximal end 66 of tube 62 through the interior space of tube 62 until the axial end of the folded-over portion exits at end hole 70 of tube distal end 68 in the form of a loop, or snare, 72. The two axial ends of the folded-over wire or other filament are positioned generally at the proximal end of tube 62. Typically, wire or other filament 64 is formed from a conventional medical grade wire material, such as polymeric (e.g. nylon) monofilament. Guide loop device 60 can include a connector assembly 74 at proximal end 66 of tubular member 40. Connector assembly can include a cap member 76 and a luer adaptor 78 threadably received within cap member 76. The threaded receipt of adaptor 78 into cap member 76 also serves to capture and hold both the proximal end of tube 62 and the two axial ends of the folded-over wire. If needed or desired, an adhesive can be applied to the threads of the adaptor 78 and/or the cap member 76 to further secure them together and fix the position of the captured portions of the tube 62 and axial ends of the folded-over wire.

Figure 6:
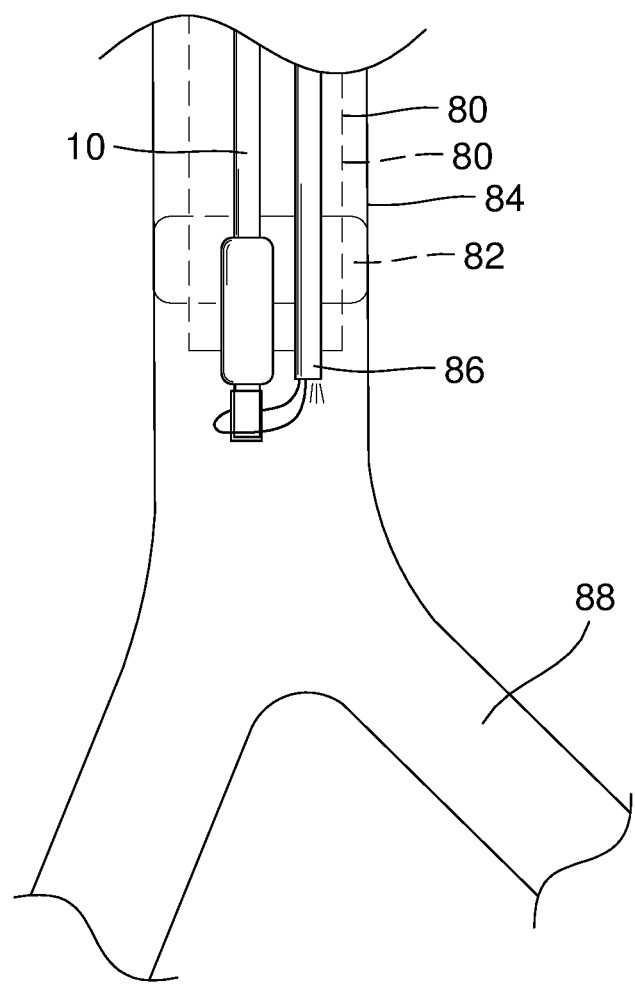
FIG. 6 provides a profile view of a trachea with an apparatus therein including a bronchoscope slidably coupled to the catheter device of FIG. 1 using the loop guide wire tool of FIG. 5 passed through the bronchoscope.
Figure 7:
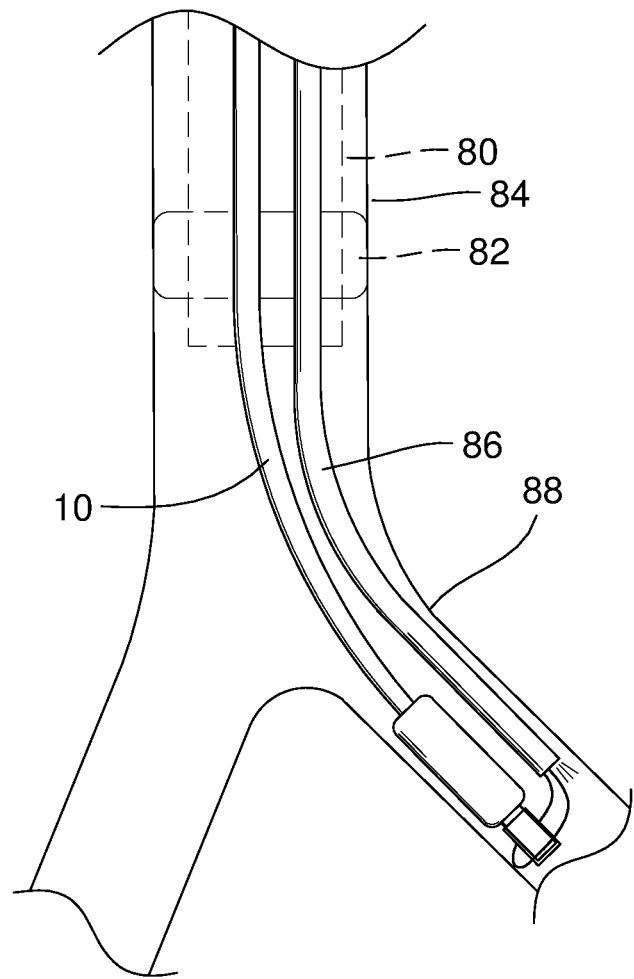
FIG. 7 provides a profile view of a trachea with the apparatus of FIG. 6 advanced into the left mainstem bronchus.

FIGS. 6 and 7 depict aspects of a preferred method of using the catheter 10, as well as other catheter devices disclosed herein. In FIG. 6, an endotracheal tube 80 with an inflated balloon 82 is positioned in the mid-tracheal region of the trachea 84 of a patient in conventional fashion. Preferably, a conventional multiport airway adapter such as the Arndt Multiport Airway Adapter, available from Cook Incorporated, of Bloomington, Ind., is used to coordinate the entry of a bronchoscope 86 and the catheter 10 into the endotracheal tube 80 through separate ports of the multiport adapter. The guide loop device 60 (FIG. 5) is advanced through the working channel or lumen of the bronchoscope 86 and wire loop 72 is disposed external and distal of the working channel. The catheter 10 is then advanced through the loop 72 to slidably connect the catheter 10 and bronchoscope 86. If desired, this connection can be established prior to introducing the bronchoscope 86/catheter 10 assembly into the patient. In addition or alternatively, visualization of this process with the bronchoscope 86 in situ in the patient can be used to facilitate the procedure. Preferably, the bronchoscope or any other endoscope to be used incorporates a well-known, articulated tip control mechanism that permits continued visualization and navigation. This can aide in both the connection of the catheter 10 and bronchoscope 86 via the loop 72, and the navigation of the apparatus as it is advanced through the endotracheal tube to the desired location in the tracheo-bronchial tree. After the catheter 10 is positioned through loop 72, guide loop device 60 can be gently retracted within the working channel to secure the connection between the catheter 10 and bronchoscope 86.

In FIG. 7, the bronchoscope 86 has entered the left mainstem bronchus 88. Without the direction provided by the bronchoscope 86 and associated guide loop device 60, entry of the catheter 10 into an area of the trachea with sharp bends, such as the left mainstem bronchus in particular, is difficult. It is also potentially damaging to the trachea due to the multiple attempts it sometimes takes to gain entrance into the desired airway, and the repetitive collisions that may occur with the tracheal wall as the endobronchial blocker catheter is maneuvered to gain entrance into the desired airway passage. After bronchoscope 86 has been maneuvered into position in the desired bronchus, the guide loop device 60 is advanced distally in the working channel of bronchoscope 86 to loosen the connection with catheter 10, and catheter 10 is withdrawn proximally a distance to free the catheter 10 from loop 72. Guide loop device 60 can then be withdrawn proximally fully into the working channel of bronchoscope 86. The leading end of the catheter 10 can then be advanced further into the bronchus, and/or the bronchoscope 86 can be withdrawn, to position the balloon 17 of catheter beyond the distal end of bronchoscope and at a location desired for inflation. Proper positioning of the balloon 17 may be visually confirmed through the bronchoscope. The balloon 17 can then be inflated using the balloon inflation assembly as previously described. When fully inflated, balloon 17 should fill the entire endobronchial lumen or other lumen to be blocked. Inflation of the balloon 17 prevents ventilation from reaching the lung areas distal to the inflated balloon.

After the physician or other healthcare provider is confident that the balloon 17 of catheter 10 has been properly positioned and inflated, the bronchoscope 86 can be removed if desired. A reservoir, such as a syringe, containing a flowable liquid therapeutic agent can then be fluidly coupled to lumen 29 of catheter 10, for example using the connector on hub extended portion 22 and opening 26. The flowable liquid therapeutic agent can then be forced under pressure through lumen 29, lumen 46, and through lumen 48 of nozzle 18, 18A to form a mist that is thrown in a direction generally distal of nozzle 18, 18A. The mist can reach and coat tissues of the lung within the region of the lung isolated by inflation of the balloon 17. If multiple regions of the lung are to be treated with the therapeutic agent(s), after deflation of the balloon 17, the catheter 10 and endoscope 86 can be withdrawn a distance, re-coupled as described above, and navigated to a different region, and the balloon inflation and misting process described above repeated.

Figure 8:
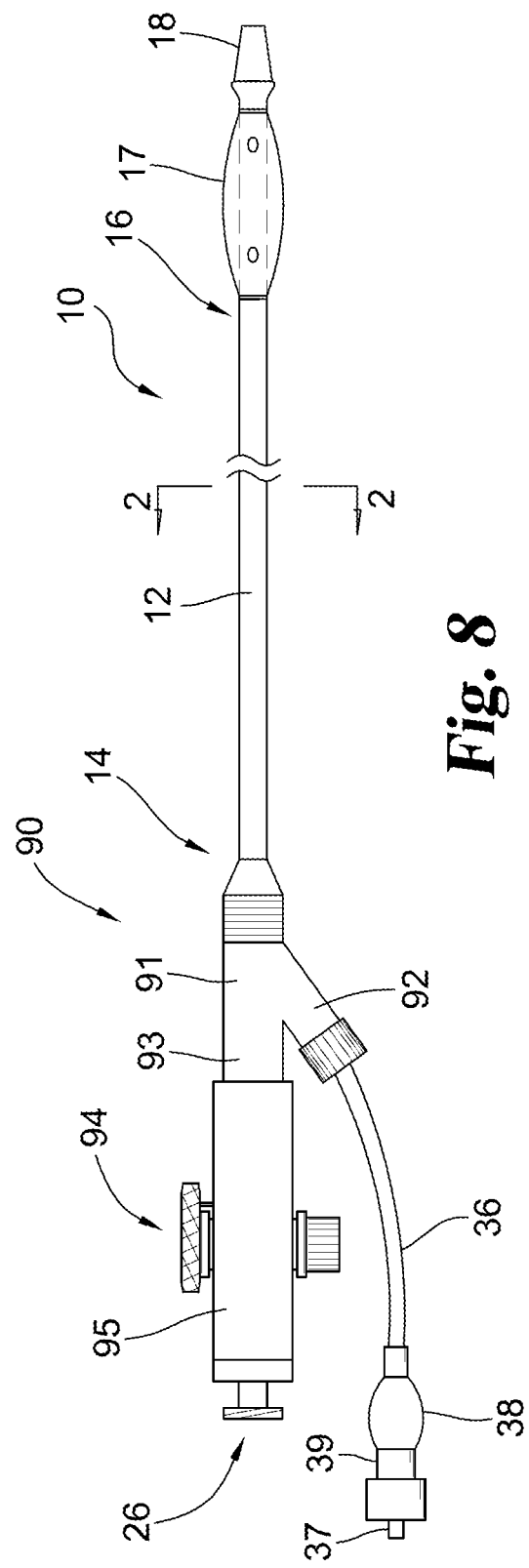
FIG. 8 provides a perspective view of a steerable catheter device.

With reference now to FIG. 8, shown is another embodiment of a misting catheter 90. Catheter 90 includes components that are the same as those for catheter 10, which are similarly numbered in FIG. 8. Catheter 90, however, has proximal features incorporating a mechanism for deflecting the distal region 16 of catheter 90. Catheter shaft 12 extends into and is affixed within a branched fitting 91 having a first branch 92 connected to balloon inflation assembly components 36, 37, 38, 39, which are in fluid communication with balloon inflation lumen 28. Fitting 91 also has a second branch 93 that is connected to a catheter deflection assembly 94.

Figure 9:
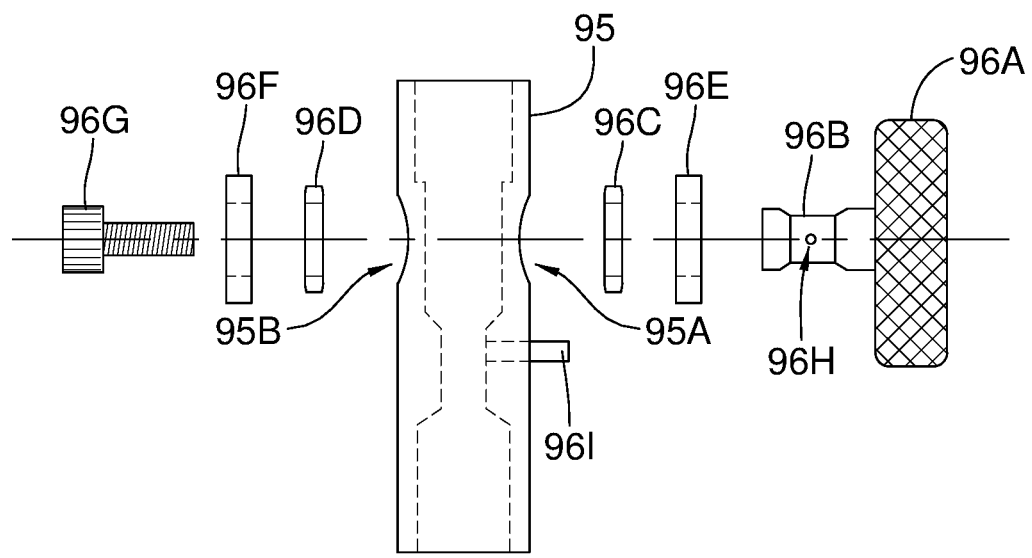
FIG. 9 provides an enlarged exploded view of a proximal housing and steering components of the catheter device of FIG. 8.
Figure 9A:
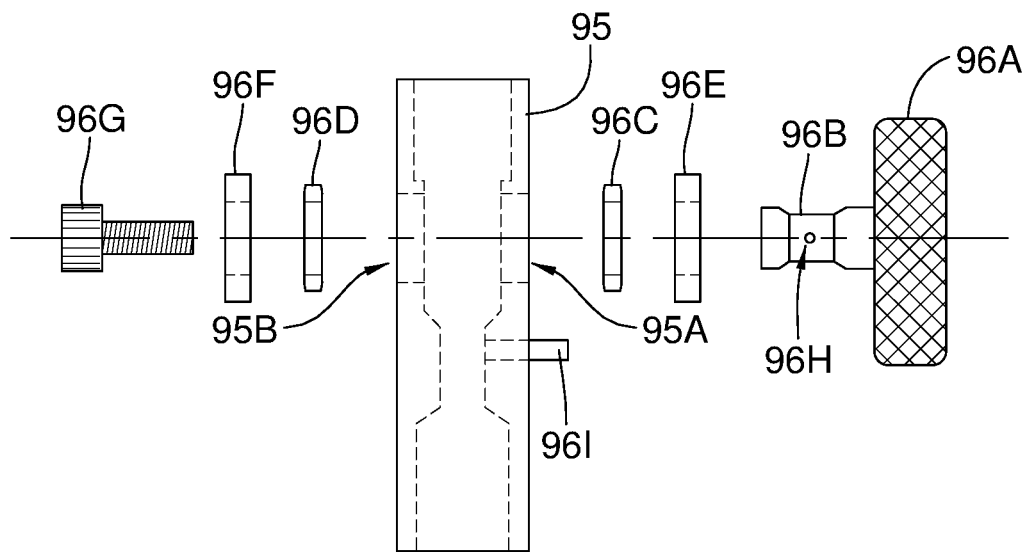
FIG. 9A provides an enlarged exploded view of an embodiment of a proximal housing and steering components of the catheter device of FIG. 8.
Figure 10:
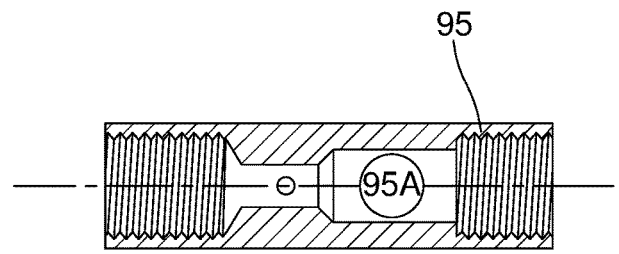
FIG. 10 provides a cross-sectional view of the proximal housing from FIG. 9.

With reference now also to FIGS. 9 and 10, assembly 94 includes a tubular housing 95. Mounted through side openings 95A and 95B in housing 95 is a control assembly 96 including an actuator wheel 96A with attached spindle 96B of a length sufficient to extend through housing 95 via openings 95A and 95B. Assembly 94 also incorporates components for sealing openings 95A and 95B around spindle 96B, while nonetheless allowing spindle 96B to rotate. For these purposes, elastomeric seal rings 96C and 96D, such as O-rings, are received around spindle 96B and positioned against the exterior surface of housing 95. Saddle washers 96E and 96F are in turn received against the exterior surfaces of seal rings 96C and 96D. These saddle washers have inner surfaces that are contoured in a curve to correspond to the curve of the outer surface of housing 95. In this manner, when washers 96E and 96F are forced against seal rings 96C and 96D, the seal rings are generally evenly compressed against the outer surface of housing 95 to form a reliable, liquid-tight seal thereagainst. In other embodiments, the outer surface of housing 95 may be flat (see FIG. 9A). In these embodiments, the inner surfaces of the saddle are contoured to be flat to correspond to the outer surface of housing 95. These seal rings are also thereby compressed against exterior surfaces of the spindle 96B, while nonetheless allowing rotation of the spindle. In preferred embodiments, this seal is sufficient to prevent any liquid leakage from openings 95A and 95B up to a pressure of about 1000 millimeters of mercury (mmHg) (about 133.3 kilopascal (kPa)) or greater, more preferably up to a pressure of about 2000 mmHg (about 266.6 kPa) or greater. To assemble, fix and compress control assembly 96 in the tubular housing 95, a screw 96G with exterior threads is provided and threads into an interior threaded bore within spindle 96B. While O-rings are illustrated in this embodiment, it will be understood that other sealing members, including other elastomeric or otherwise compressible sealing members, such as gaskets, can be used in other embodiments to establish and maintain a seal between an opening(s) in an actuator housing and a spindle or other actuator component extending through the opening(s). Additionally, while in the illustrated embodiments the housing 95 is a tubular housing with a generally curved wall presenting a circular cross-sectional outer profile, it will be understood that other housing shapes, including those that have one, two or more generally flat outer wall surfaces, can be used. Illustratively, an actuator housing can have at least first and second flat outer walls presenting flat outer wall surfaces, and the openings for a spindle such as spindle 96B can extend through the flat outer walls, with the O-rings, gaskets or other elastomeric seal elements compressed against the flat outer wall surfaces to create the liquid tight seal as discussed herein. Likewise, it will be understood that in additional embodiments in which a deflecting wire is used, other types of actuators, including for example other rotatable actuators or axially-sliding actuators, can be attached to the deflecting wire and permit axial tensioning and detensioning of the deflecting wire.

A deflecting wire extending through lumen 30 of shaft 12 (replacing the stiffening wire of catheter 10 discussed above) is threaded through opening 96H in spindle 96B and wound around spindle 96B to attach the wire to the spindle. This deflecting wire is slidably received through housing 95, branched fitting 91 and within lumen 30 in a proximal region of shaft 12, but bonded or otherwise fixed in position within lumen at or proximate to the distal end of shaft 12. For example, an adhesive may be used to bond the deflecting wire in place within lumen 30 at or proximate to the distal end of shaft 12. In this fashion, control wheel 96A can be rotated to take up, or to release, segments of the deflecting wire to adjust the tension applied to the deflecting wire and controllably deflect the distal region of the catheter 90. In a preferred embodiment, an interior surface of wheel 96A is provided with a groove that circumscribes less than 360 degrees, and a pin 96I mounted in housing 95 is received within and travels within the groove as wheel 96A is rotated, and limits the extent of possible rotation of wheel 96A by striking end walls of the groove on either of its ends. In this and other embodiments disclosed herein, deflection of the distal region of the catheter device can be used to facilitate steering of the distal region of the catheter device to a desired location. In addition or alternatively, deflection of the distal region of the catheter device can be used to controllably alter the direction of throw of a mist from a misting nozzle when such a nozzle is present.

Catheter 90 has a proximal opening or port 26 that fluidly communicates with the interior of housing 95. In the illustrated embodiment, the port 26 fluidly communicates with lumen 29 of shaft 12 through the interior of housing 95 such that liquid passed into port 26 enters the interior of housing 95 and contacts and flows around spindle 96B and the attached deflecting wire and then enters lumen 29 exposed to the interior of housing 95. The seal rings 96C and 96D, compressed against the exterior surface of the housing 95 and the exterior surface of the spindle 96B by the washers 96E and 96F, prevent the leakage of the liquid out of the side openings 95A and 95B. It will be understood, however, that other arrangements for flow of liquid passed into port 26 can also be provided, including arrangements that isolate the flow from contact with spindle 96B.

Catheter 90 can be used to access and treat lungs passageways or other passageways or cavities of the body in conjunction with an endoscope such as a bronchoscope as discussed above in connection with catheter 10. Thus, the catheter 90/bronchoscope assembly can incorporate two modes for steering, one incorporated in the bronchoscope and one incorporated in the catheter 90. This provides additional control in accessing regions of the lung, including deep regions. Alternatively, catheter 90 can be steered through the passageway(s) independently of connection to the bronchoscope or other endoscope. After placement in a desired location, the balloon 17 can be inflated, and regions distal to the inflated balloon treated with a misted therapeutic liquid, as discussed herein.

A catheter having the construction of catheter 90 was used in an experiment investigating the effectiveness of catheter 90 for delivering a cell suspension to a region of a lung. The experiment detected levels of cells present in a lung region after a cell suspension was delivered to the lungs of a pig using a bronchial infusion from catheter 90. The results were compared to the levels of cells present in the lung region of a pig after an intravenous (IV) injection of a corresponding cell suspension. A cell suspension was prepared that included $100 \times 10^6$ human muscle derived cells (MDCs), fluorescently labeled with Vybrant® DiR lipophilic fluorescent tracer (0.5 µM), washed and resuspended in 10 mL PBS. The cell suspension was aliquoted into four 2.5 mL syringes for delivery through catheter 90. The cell suspension (10 mL) was then infused into four different areas of the lungs through the lumen of the catheter 90 via four separate 2.5 mL injections. After delivery of the nozzle 18 of catheter 90 to a selected region of the lung, one of the 2.5 ml syringes was connected to port 26 and the plunger depressed to force the cell suspension through catheter 90 and out of its misting nozzle 18 as a mist. The selected regions of the lung included the left caudal lobe, the accessory lobe, and the right cranial lobe. The infusion time ranged from 7 to 14 seconds. The infusion pressure ranged from 6-150 mmHg. Subsequent fluorescence imaging detected profuse levels of the MDCs in the regions of the lung where the cell suspension was sprayed using catheter 90. The levels of MDCs present resulting from the bronchial infusion from catheter 90 was much greater than the levels of MDCs in the corresponding lung regions that resulted from the IV injection.

Figure 11:
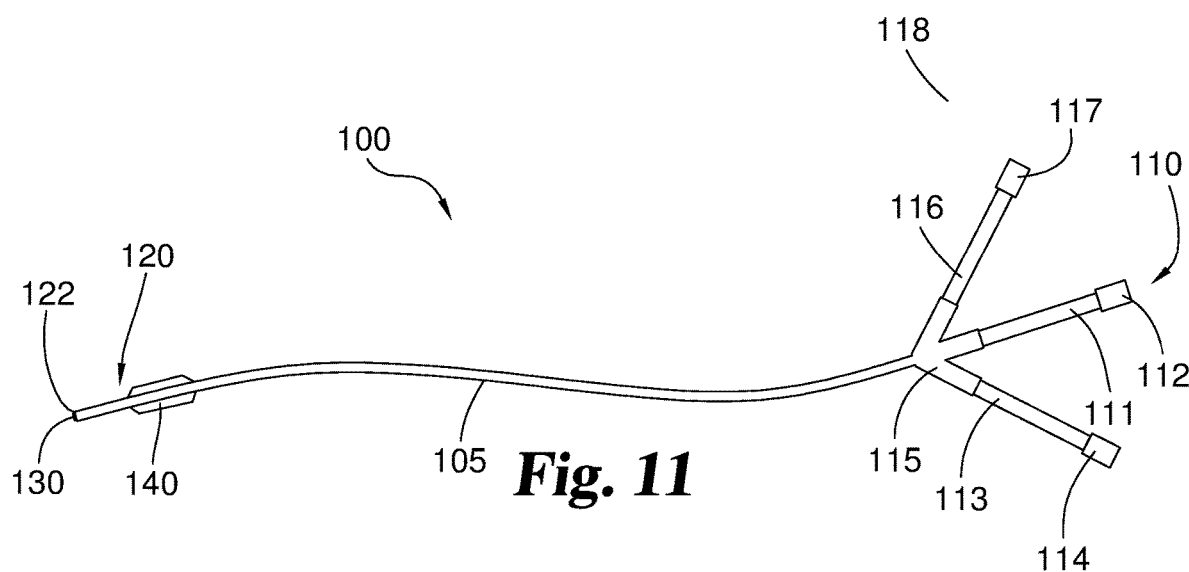
FIG. 11 provides a perspective view of another catheter device.

FIG. 11 illustrates another embodiment of a catheter device 100. Catheter device 100 includes a catheter shaft 105. Catheter device 100 has a proximal end 110 and a distal end 120. A proximal hub 115 is attached to catheter shaft 105 at proximal end 110. In the embodiment shown, proximal hub 115 is branched, creating three separate lumens therein that terminate in respective openings. A first of the openings is in fluid communication with an injection extension 111. An injection port 112 is connected to the end of injection extension 111. A second of the openings in proximal hub 115 is in fluid communication with a balloon inflation extension 113. A balloon inflation port 114 is connected to the end of inflation extension 113. The other opening of proximal hub 115 is connected to a wire guide extension 116 that includes a wire guide port 117.

In some embodiments, injection port 112 and inflation port 114 are constructed so they may be connected to a syringe or other pressurized fluid input device. The syringe or other input device may provide air or liquid that is to be introduced into catheter 100. In some embodiments, injection port 112 and inflation port 114 are equipped with luer lock or other threaded connectors. A pressure gauge having an inlet and outlet may also have its outlet connected to injection port 112 and its inlet connected to the syringe or other input device. In this way, the pressure gauge is operable to monitor the injection pressure of a flowable biologic, therapeutic or other flowable material passed into injection port 112.

Distal end 120 of catheter device 100 includes a tip 122 at the distal-most point of catheter shaft 105. Some embodiments include a misting nozzle 130 at tip 122. An inflatable balloon 140 is positioned around catheter shaft 105 at distal end 120. Inflatable balloon 140 is located proximal of misting nozzle 130.

Misting nozzle 130 may be any structure that provides a mist from a flow of liquid, including misters, nebulizers, or atomizers. Misting nozzle 130 may provide the mist in any geometry that produces a spray. For example, in some embodiments the misting nozzle may produce a fine nozzle spray pattern, a wide cone spray pattern, a hollow cone spray pattern, or a flat fan spray pattern.

Figure 12:
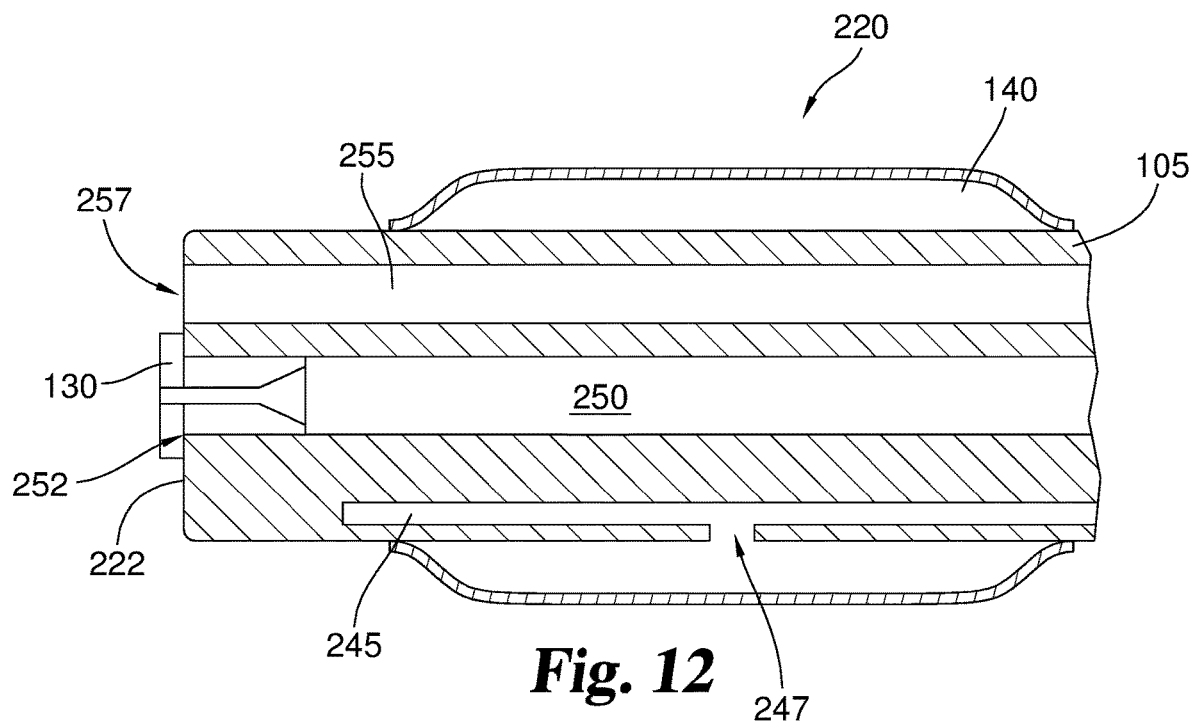
FIG. 12 provides a cross-sectional view of an embodiment of a distal end of the catheter device of FIG. 11 with an injection lumen, a guide lumen, a balloon inflation lumen, and a misting nozzle.

FIG. 12 illustrates an embodiment of a distal end 220 of catheter device 100. Distal end 220 includes a distal tip 222, a balloon inflation lumen 245, an injection lumen 250, and a guide lumen 255. Injection lumen 250 and guide lumen 255 extend through catheter 100. Injection lumen 250 ends at injection lumen distal opening 252 and guide lumen 255 ends at guide lumen opening 257.

Injection lumen 250 is large enough to allow passage of liquid or other material, such as biologic material, used for treatment of a portion of the body. Injection lumen 250 extends from the distal end 220 of catheter 100 to the proximal end of catheter 100 where it is in communication with proximal hub 115 and injection port 112. The treatment material is passed into injection port 112 and then travels through injection lumen 250 to be ejected out of injection lumen opening 252 and applied to a desired portion of the body.

In some embodiments, distal end 220 includes a misting nozzle 130 in fluid communication with injection lumen 250. A stem or similar portion of misting nozzle 130 is inserted inside injection lumen 250 through opening 252 to secure misting nozzle 130 to distal end 220. The distal end of misting nozzle 130 extends distally past distal tip 222. Liquid is passed into injection lumen 250 and flows through catheter 100 until it reaches misting nozzle 130. Misting nozzle 130 provides a mist from the liquid in injection lumen 250 and directs the mist distally from catheter 100 to a desired location.

Guide lumen 255 is large enough to allow passage of a wire guide or in some embodiments a guide loop device. A wire guide or a guide loop device may be inserted through guide lumen 255 and extended past the distal tip 222 of catheter 100. If a guide wire is used for positioning, standard wire guide placement methods with the aid of a scope may be used to position catheter 100 at the desired location within the body. If a guide loop device is used (e.g. as depicted in FIG. 5), the guide loop is passed through guide lumen so the loop portion extends distally from guide lumen opening 257. The loop can then be positioned around an endoscope. The endoscope can be used to guide catheter 100 to the desired location within the body as discussed herein.

Inflatable balloon 140 is positioned around shaft 105. Balloon inflation lumen 245 is in communication with inflation port 114 at the proximal end of catheter 100 and extends through catheter 100, at least to the position of inflatable balloon 140. An inflation passage 247 provides fluid communication between balloon inflation lumen 245 and the interior of inflatable balloon 140. A fluid, such as air, water or another aqueous medium, may be introduced at inflation port 114, travel through inflation extension 113 and into balloon inflation lumen 245. The fluid then travels through balloon inflation lumen 245 to inflation passage 247 where it is introduced into the interior of inflatable balloon 140, causing inflatable balloon 140 to inflate.

Inflatable balloon 140 may be used to isolate a portion of the body for treatment. For example, catheter 100 may be inserted into the lungs and inflatable balloon 140 inflated to isolate a lobe or other region of the lung for treatment. Inflatable balloon 140 blocks or hinders the material used for treatment from entering other lobes or regions of the lungs, resulting in an efficient delivery of treatment material.

Figure 13:
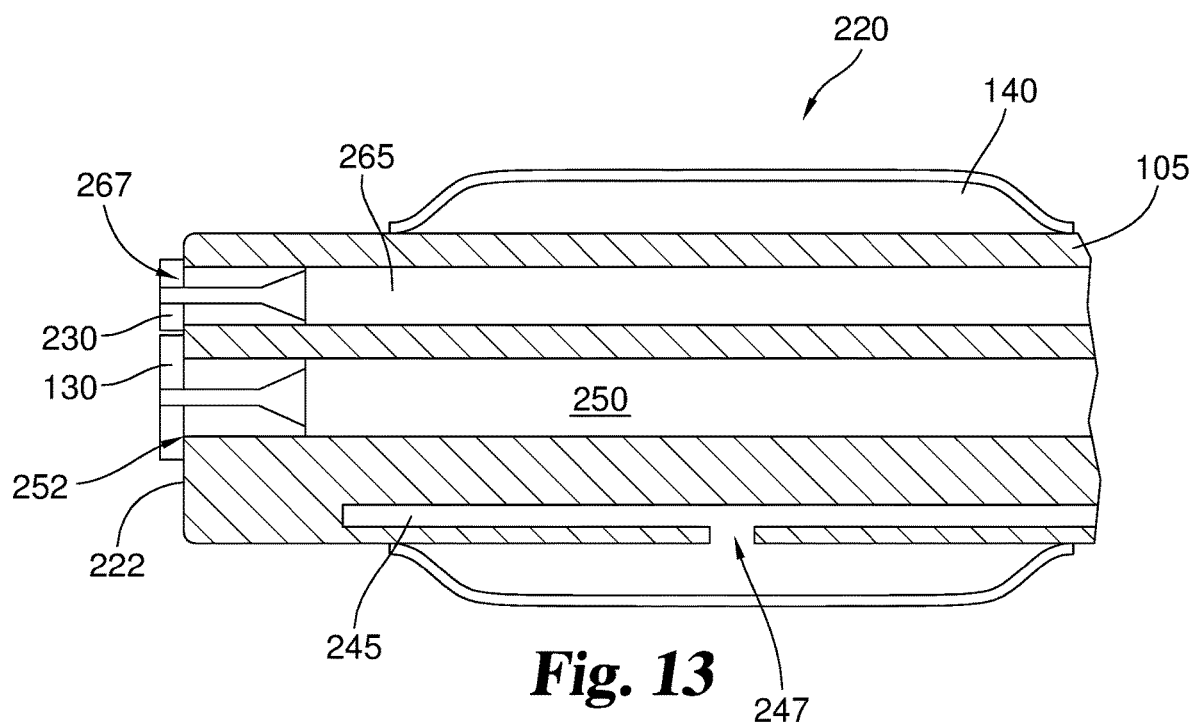
FIG. 13 provides a cross-sectional view of an embodiment of a distal end of the catheter device of FIG. 11 with two injection lumens, a balloon inflation lumen, and two misting nozzles.

FIG. 13 illustrates an alternative embodiment of the catheter device 100 shown in FIG. 12. In this embodiment, guide lumen 255 is replaced with a second injection lumen 265. Injection lumen 265 extends from the distal end 220 of catheter 100 to the proximal end of catheter 100, where it is in communication with proximal hub 115 and port 117. A different injection material than the injection material that is introduced through injection lumen 250 may be introduced into injection lumen 265.

In some embodiments, distal end 220 may include a second misting nozzle 230 in fluid communication with injection lumen 265. In some embodiments, the misting nozzle 230 can have the same construction as misting nozzle 130. In other embodiments, misting nozzle 230 can have a different construction from misting nozzle 130, for example constructed to produce a mist having a different character than a mist produced by misting nozzle 130. The different character in some embodiments can include a mist having a differing average droplet size (e.g. at the same input pressure with the same liquid into nozzles 130 and 230) and/or a differing pattern of spray. A stem or similar portion of misting nozzle 230 is inserted inside injection lumen 265 through opening 267 to secure misting nozzle 230 to distal end 220. The distal end of misting nozzle 230 extends distally past distal tip 222. Liquid is passed into injection lumen 265 and flows through catheter 100 until it reaches misting nozzle 230. Misting nozzle 230 provides a mist from the liquid in injection lumen 265 and directs the mist distally from catheter 100 to a desired location.

The second nozzle 230 may be used for delivery of a different substance than the substance delivered by nozzle 130. As an example, in some instances, it may be advantageous to deliver a cell suspension (e.g. including any of the types of cells identified herein, or their mixture) through one of nozzles 130 and 230 and a second material, for example a cell growth or support substance such as a cell culture medium and/or a matrix material, through the other of nozzles 130 and 230. A wide variety of cell culture media are known. A variety of matrix materials to support cell survival and/or growth are also known and include, illustratively, natural or synthetically produced polymeric substances such as collagen, elastin, fibronectin, laminin, proteoglycans, heparin sulfate, chondroitin sulfate, keratin sulfate, hyaluronic acid, or any other material that may enhance the therapy provided by the cells. The cell growth or support substance may be included in an aqueous or other liquid medium (e.g. a solution or suspension) that is more viscous than the cell suspension. Therefore, the medium including the cell growth or support substance may require a higher pressure for delivery through the misting nozzle and/or may generate greater shear forces when delivered through the misting nozzle than the cell suspension delivered through the other, separate, misting nozzle. Such pressure and/or shear forces experienced by the cell growth or support substance delivery medium may cause damage to the cells if they were included in the cell growth or support substance medium. Accordingly, by delivering the cell growth or support delivery medium through a separate misting nozzle than the misting nozzle used to deliver the cell suspension, the risk of damaging the cells can avoided or decreased while delivering the cell suspension and cell growth or support substance at the same time. In some forms, when so delivered from nozzles 130 and 230 at the same time, the cells and the cell growth or support substance can intermix in their mist forms to form an intermixed mist prior to depositing on a target tissue surface region (e.g. a surface on the interior of a lung) and/or can intermix after they contact the target tissue surface region. For purposes of forming an intermixed mist of these or other types of delivered media prior to deposition on the target tissue surface region, the spray pattern of the nozzle 130 can at least partially overlap the spray pattern of nozzle 230 and in certain preferred embodiments the positions of nozzles 130 and 230 can be fixed relative to one another to maintain a consistent overlap of their respective spray patterns during use of catheter device 100.

Other embodiments in which different flowable liquid media are separately delivered through misting nozzles 130 and 230 will also be advantageous. For example, in some embodiments, the flowable liquid media to be separately delivered can be combinable with each other to react to produce a solid material (nonflowable) or a more viscous flowable material than the media prior to their combination. Illustratively, a first flowable liquid medium can include a polymerizable substance (e.g. a monomer or oligomer) and the a second flowable liquid medium can include a polymerization initiator such as a polymerization catalyst to cause polymerization of the polymerizable substance. In other embodiments, a first flowable liquid medium can include a gellable polymeric substance and a second flowable liquid medium can include or act as a gelling agent. In some embodiments, the gellable polymeric substance of the first flowable liquid medium can respond to a change in temperature to form a gel and the second flowable liquid medium can be at a different temperature than the first flowable liquid medium (e.g. a higher or lower temperature) so that upon mixing after exit from nozzles 130 and 230 the gellable substance is caused to change temperature and gel. In one such embodiment, the first flowable liquid medium can include gelatin or another polymeric substance that forms thermoreversible gels upon cooling and the second flowable liquid medium can be at a temperature lower than the first flowable liquid medium so that when the two media are mixed after exiting the nozzles the gelatin or other thermoreversible gel forming polymeric substance is induced to gel. Additionally or alternatively, the gellable polymeric substance of the first flowable liquid medium can respond to a change in pH to form a gel and the second flowable liquid medium can be at a different pH than the first flowable liquid medium (e.g. a higher or lower pH) so that upon mixing after exit from nozzles 130 and 230 the gellable substance is caused to undergo pH-induced gelling. In one such embodiment, the first flowable liquid medium can include collagen and have an acidic pH at which the collagen does not gel, and the second flowable liquid medium can have a basic pH and/or include a buffer to raise the pH of the first flowable liquid medium when mixed therewith to induce gelling of the collagen. Still further additionally or alternatively, the first liquid flowable medium can include a gellable polymeric substance that forms a gel when combined with a molecular species included in the second liquid flowable medium so that upon mixing of the first and second media after exit from nozzles 130 and 230 the gellable substance is caused to react with the molecular species and gel. In some such embodiments, the molecular species can be an anionic or cationic molecule that causes the gellable substance to gel when mixed therewith. Illustratively, the gellable substance can be a natural (e.g. alginate) or synthetic anionic polymer and the molecular species can be a multivalent (e.g. divalent or trivalent) cation, for example calcium, that complexes with the polymer to form a gel. In other forms, the gellable substance can be a natural (e.g. chitosan) or synthetic cationic polymer and the molecular species can be a multivalent (e.g. divalent or trivalent) anion, for example tripolyphosphate, that complexes with the cationic polymer to form a gel. These and other gel or solid-forming combinations of first and second media to be delivered through nozzles 130 and 230 will be apparent to those of ordinary skill in the art from the descriptions herein. As well, it will be understood that the first and/or the second medium in these embodiments can include another substance, for example cells or other therapeutic substances identified herein, to be incorporated in the formed gel or solid on the target lung interior tissue surface or other target body cavity tissue surface. In some cases where the therapeutic substance includes cells, the formed solid or gel substance can support the survival and/or growth of the cells and/or can entrain the cells to facilitate retention of the cells in the region of delivery. In some cases where the therapeutic substance includes a drug or other pharmaceutical agent (e.g. any of those identified herein), the formed solid or gel can entrain the pharmaceutical agent and serve as a localized depot for sustained release of the pharmaceutical agent, for example releasing the pharmaceutical agent over a period of at least about 1 day, at least about 3 days, or at least about 7 days, but in any of these cases not exceeding about 6 months in some embodiments or not exceeding about 30 days in other embodiments.

As noted above, in some embodiments, misting nozzle 130 may be operated at the same time as misting nozzle 230, so that the flowable media employed may be delivered at the same time. In other embodiments, misting nozzles 130, 230 may be operated at different times but nonetheless during the same insertion of the catheter that carries them. For example, a first medium including cells (e.g. any of those identified herein) can be delivered through nozzle 130 and then subsequently a second medium including a cell growth or support substance (e.g. any of those identified herein) can be delivered through nozzle 230 to combine with the cells on a target interior lung or other tissue surface to be treated. Alternatively, a first medium including a cell growth or support substance (e.g. any of those identified herein) can be delivered through nozzle 130 and then subsequently a second medium including cells (e.g. any of those identified herein) can be delivered through nozzle 230 to combine with the cell growth or support substance on a target interior lung or other tissue surface to be treated. Processes in which both simultaneous delivery of different substances through nozzles 130 and 230 and sequential delivery of those different substances through nozzles 130 and 230 are of course also contemplated. Thus, reference herein to simultaneous delivery of different substances through nozzles 130 and 230 should be understood to include processes in which the substances are delivered partially or completely simultaneous, and reference herein to sequential delivery of different substances through nozzles 130 and 230 should be understood to include processes in which the substances are delivered partially or completely sequentially.

Figure 14:
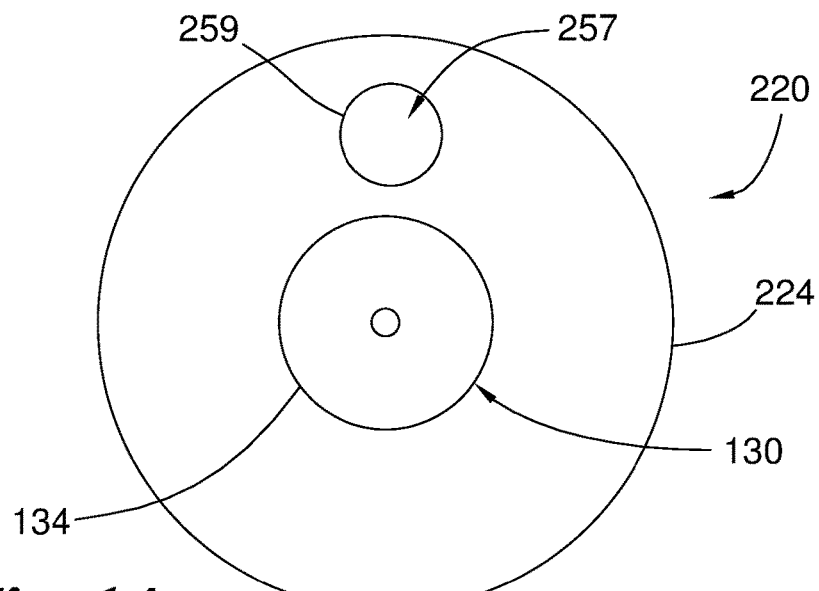
FIG. 14 provides a longitudinal view of distal end of the catheter device shown in FIG. 12.

FIG. 14 shows distal end 220 from a side view in a longitudinal direction. This view shows the longitudinal profiles of misting nozzle 130 and guide lumen opening 257. The distal end 220 of the catheter shaft has an outer profile 224 formed by the outer perimeter of distal end 220. Misting nozzle 130 has an outer profile 134 defined by the outermost perimeter of misting nozzle 130. Guide lumen opening 257 has an outer profile 259 defined by the outermost perimeter of opening 257. As shown in FIG. 14, when viewed from a longitudinal direction, the outer profile 134 of misting nozzle 130 does not overlap the outer profile 259 of guide lumen opening 257. Also, outer profile 134 of misting nozzle does extend beyond the outer profile of distal end 220. Thus, catheter 100 can be translated along a guidewire extending through guide lumen 255 and out of opening 257 while avoiding contact between the guidewire and misting nozzle 130. Alternatively, a loop of a guide loop device can be extended out of and distal of opening 257 without contacting misting nozzle 130.

In the embodiment shown in FIG. 12, both the injection lumen opening 252 and guide lumen opening 257 are found at distal tip 222 of catheter 100. However, in other embodiments, one or both of openings 252, 257 may be positioned at staggered locations on catheter 100, not necessarily at distal tip 222. For example, the portion of catheter 100 in which guide lumen 255 is positioned may not extend as far as the portion of catheter 100 in which injection lumen 250 is positioned. Therefore, guide lumen opening 257 is not located at distal tip 222, but guide lumen 257 still extends through catheter 100. Even if both openings 252, 257 are not located at distal tip 222, when catheter 100 is viewed from a longitudinal direction, as shown in FIG. 14, in preferred forms, the outer profile 134 of misting nozzle 130 does not overlap the outer profile 259 of guide lumen opening 257.

Figure 15:
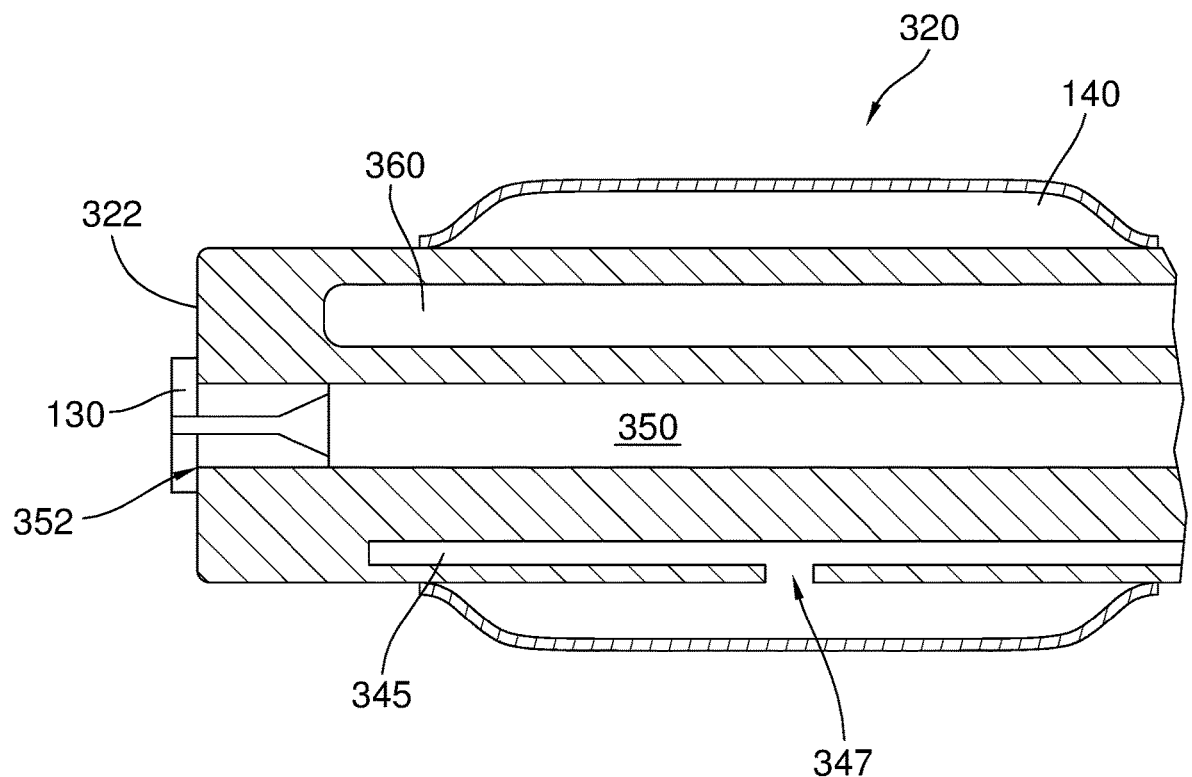
FIG. 15 is a cross-sectional view of an embodiment of a distal end of the catheter device of FIG. 11 with an injection lumen, a tip deflection or wire guide lumen, a balloon inflation lumen and a misting nozzle.

FIG. 15 illustrates an alternative embodiment of a distal end 320 of catheter device 100. Distal end 320 includes a distal tip 322, a balloon inflation lumen 345, an injection lumen 350, and a tip deflecting wire lumen 360. Injection lumen 350 extends through catheter 100, creating an injection lumen opening 352. Tip deflecting wire lumen 360 does not extend through the entire length of catheter 100 and is closed before reaching distal tip 322 of catheter 100. Distal end 320 is similar to distal end 220; however, the structure which is used to position catheter 100 within the body is different from the structure used in distal end 220. Instead of having a guide lumen 255 for insertion of a guide wire or a guide loop device, distal end 320 includes a tip deflecting lumen 360 into which a tip deflecting wire 362 is inserted. A user may control the position of tip deflecting wire 362 and cause the distal end of wire 362 to deflect, in certain embodiments up to 90 degrees or more in either direction. Movement of tip deflecting wire 362 adjusts the position of distal end 320 as distal end 320 moves along with tip deflecting wire 362. An operator may control the deflection of the tip deflecting wire to guide catheter 100 through the body and position distal end 320 at a desired location.

Figure 16:
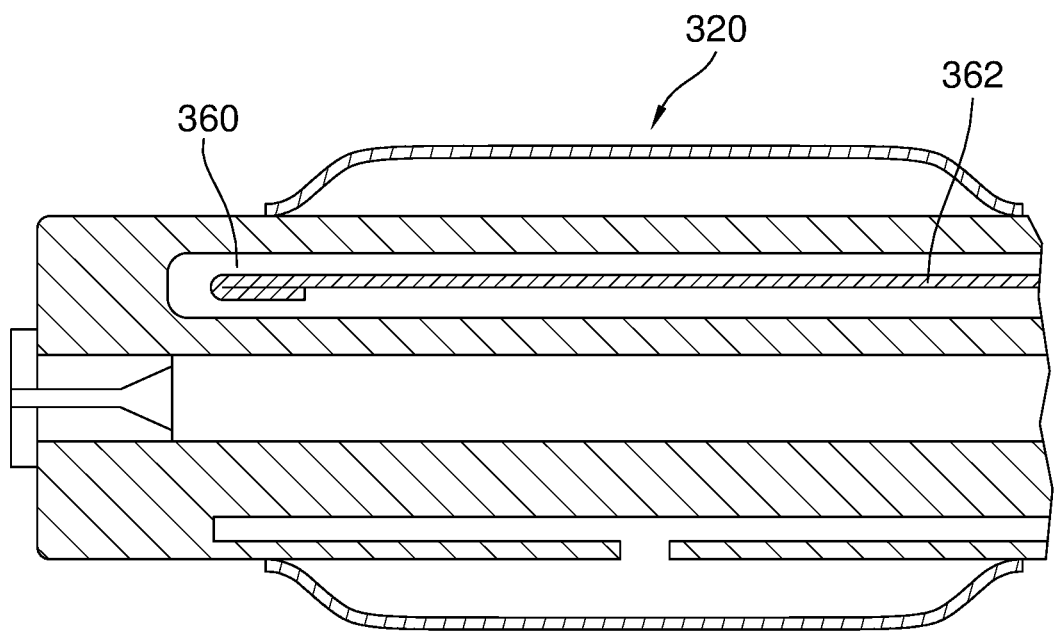
FIG. 16 is a cross-section view of the distal end of the catheter device of FIG. 4 with a tip deflecting wire inserted into a tip deflecting lumen.

FIG. 16 shows a deflecting wire 362 inserted into tip deflecting wire lumen 360. Deflecting wire 362 extends through the length of tip deflecting wire lumen 360 to the closed distal end. At the distal end, deflecting wire 362 is bent into a U-shape so a portion of the end deflecting wire 362 is directed proximally. The deflecting wire 362 can be fixedly attached to the catheter shaft 105 in a distal region of shaft 105 in any suitable manner, including for example by use of an adhesive, knotting, or otherwise. Additionally, shaft 105 can be fabricated from multiple segments of tubing, for example having a first segment extending from the proximal end of shaft 105 to just proximal to inflatable balloon 140, a second segment bonded to the first segment and extending under inflatable balloon 140, and a third segment bonded to the second segment and located distal to inflatable balloon 140. In such a multiple-segment fabricated shaft 140, the deflecting wire can for example extend through the first and second segments of shaft 105 and exit a distal end opening of the second segment, providing an extended wire portion that can be knotted and/or tucked into another distal end opening of the second segment. The third shaft segment can then be bonded onto the second segment and over the extended wire portion. The second and/or third segment of such a shaft 105 can be made from a polymeric material that is softer (lower in durometer) than the first segment, to provide increased flexibility in the distal region of shaft 105. These and other arrangements for the fixed attachment of the deflecting wire at the distal region of shaft 105, to enable deflection of the distal region of shaft 105 when the deflecting wire is pulled proximally, are contemplated as being suitable for the embodiments disclosed herein.

Figure 17:
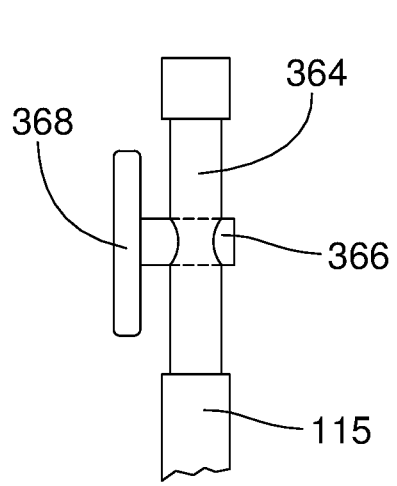
FIG. 17 is a front view of an actuator housing.
Figure 18:
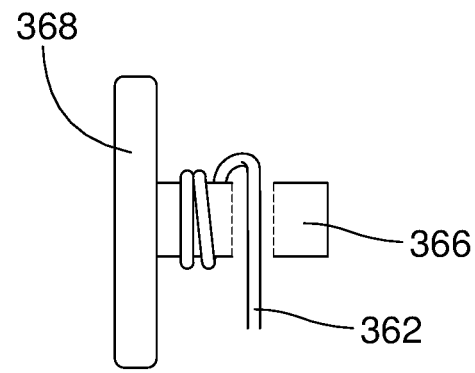
FIG. 18 is a front view of a pin and control piece from the actuator housing of FIG. 17.

The proximal end of deflecting wire 362 is attached to an actuating member within an actuator housing 364 (see FIG. 17). Actuator housing 364 may be connected to proximal hub 115 of catheter device 100 in place of wire guide extension 116 and port 117 (as seen in FIG. 11). In the illustrated embodiment, the proximal end of deflecting wire 362 is attached to an actuating member comprised of a rotatable spindle 366 inserted through an opening in actuator housing 364. Spindle 366 has a through hole 367 through which deflecting wire 362 may be passed and wound around rotatable spindle 366 (see FIG. 18). A control piece 368 for rotating rotatable spindle 366, such as a wheel, is accessible on the outer portion of actuator housing 364. Other details of the actuator housing 364 and its associated actuating components can, for example, be the same as described hereinabove in conjunction with the catheter deflection assembly 94 of FIGS. 8-10.

A user may adjust the position of the distal end 120 of the catheter device 100 by using control 368 to rotate rotatable spindle 366. If control piece 368 is a wheel, the user rotates the wheel to cause deflecting wire 362 to either wind around rotatable spindle 366 or to unwind from rotatable spindle 366 depending on the direction of rotation. Winding or unwinding deflecting wire 362 around rotatable spindle 366 tensions or detensions deflecting wire 362. If deflecting wire 362 is wound further onto spindle 366 to add tension, deflecting wire 362 starts to curve and forces on distal tip 120 and catheter 100 to deflect along with wire 362. If the deflecting wire 362 is unwound from spindle 366, the distal region of wire 362 straightens and the distal tip 120 region of catheter 100 moves to a straighter orientation. The user may selectively wind and unwind deflecting wire 362 around rotatable spindle 366 using control piece 368 to aid in steering catheter device 100 to a desired position in a patient's body.

As shown in FIGS. 15-16, in some embodiments, distal end 320 includes a misting nozzle 130 located at the end of injection lumen 350 near injection lumen opening 352. Misting nozzle 130 in this embodiment is similar to misting nozzle 130 from FIG. 12. A portion of misting nozzle 130 is inserted inside injection lumen 350 through opening 352 to secure misting nozzle 130 to distal end 320. The distal end of misting nozzle 130 extends distally past distal tip 322.

Similar to the embodiment shown in FIG. 12, inflatable balloon 140 is positioned around tube 105 and may be either inflated or uninflated. Balloon inflation lumen 345 is in communication with inflation port 113 at the proximal end of catheter 100 and extends through catheter 100, at least to the position of inflatable balloon 140. An inflation passage 347 provides fluid communication between balloon inflation lumen 345 and the interior of inflatable balloon 140. A fluid, such as air, water or another aqueous liquid, may be introduced at inflation port 114, travel through inflation extension 113 and into balloon inflation lumen 345. The fluid then travels through balloon inflation lumen 345 and through inflation passage 347 whereupon it is introduced into the interior region of inflatable balloon 140, causing inflatable balloon 140 to inflate.

Figure 19:
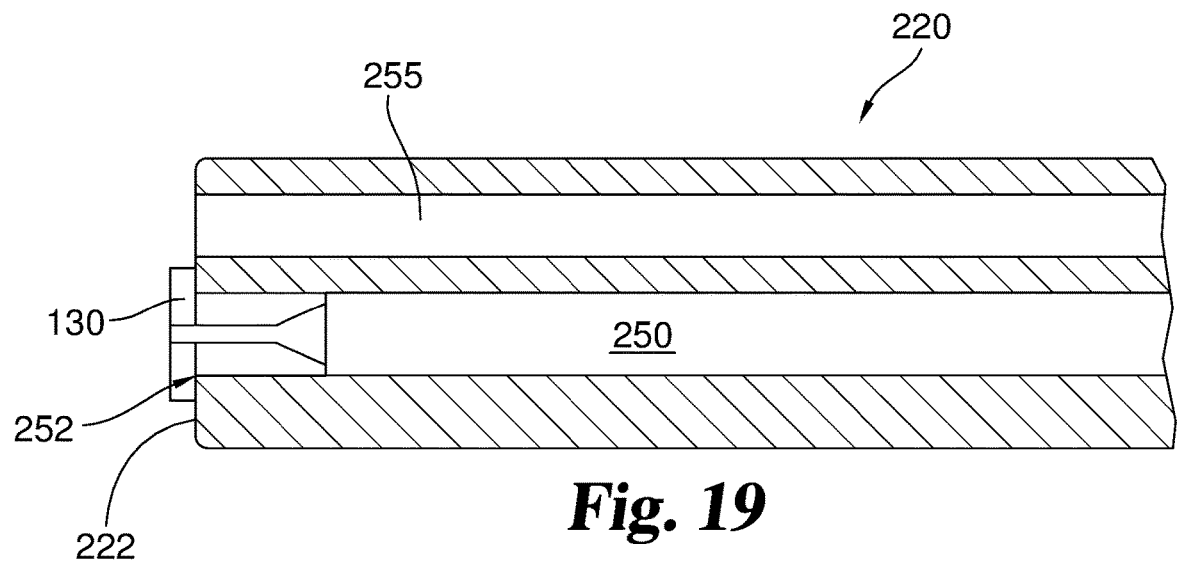
FIG. 19 is a cross-section view of an embodiment of a distal end of the catheter device of FIG. 11 with an injection lumen, a guide lumen and a misting nozzle.
Figure 20:
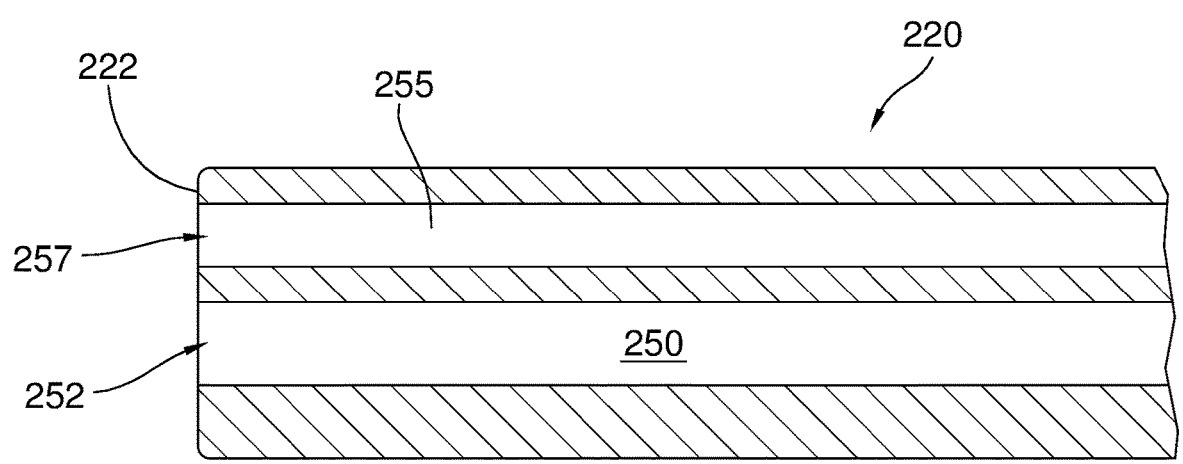
FIG. 20 is a cross-section view of an embodiment of a distal end of the catheter device of FIG. 11 with an injection lumen and a guide lumen.

FIGS. 19-20 illustrate alternative embodiments of distal end 220 that include only two lumens rather than three. In these embodiments, distal end 220 includes a distal tip 222, an injection lumen 250 and a guide lumen 255. However, there is no inflatable balloon 140 or balloon inflation lumen 245. Similar to the embodiment shown in FIG. 12, guide lumen 255 is large enough to allow passage of a wire guide or a guide loop device that is used to position catheter 100 in the location of the body that needs treatment. Injection lumen 250 is large enough to allow introduction and passage of a solid material or fluid used for treatment.

In the embodiment shown in FIG. 19, distal end 220 includes misting nozzle 130 inserted into injection lumen 250 through injection lumen opening 252. In an alternative embodiment shown in FIG. 20, misting nozzle 130 is not present, so any liquid or other flowable material injected into injection lumen 250 can still exit catheter 100, but is not ejected as a mist.

Figure 21:
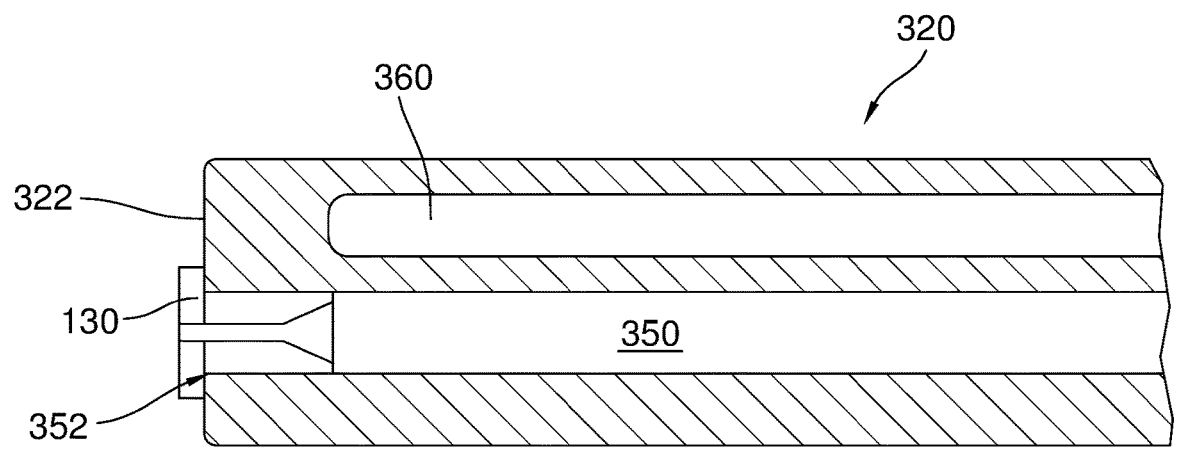
FIG. 21 is a cross-section view of an embodiment of a distal end of the catheter device of FIG. 11 with an injection lumen, a tip deflecting wire lumen and a misting nozzle.
Figure 22:
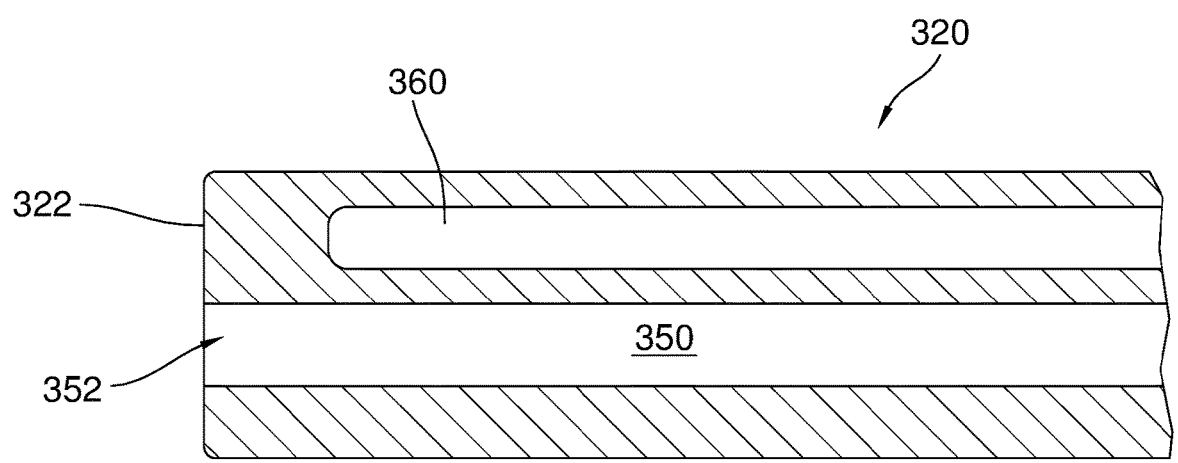
FIG. 22 is a cross-section view of an embodiment of a distal end of the catheter device of FIG. 11 with an injection lumen and a tip deflecting wire lumen.

The embodiments shown in FIGS. 21-22 are also double lumen catheters, and include an injection lumen 350 and a tip deflecting wire lumen 360. There is no inflatable balloon 140 or balloon inflation lumen 245. The catheters from FIGS. 21-22 include and are positioned using a tip deflecting wire 362 and an associated catheter deflection assembly (see e.g. FIGS. 8-10) in the same method as described above. Distal end 320 may include a misting nozzle 130 (see FIG. 21) or may lack a misting nozzle 130 (see FIG. 22).

Figure 23:
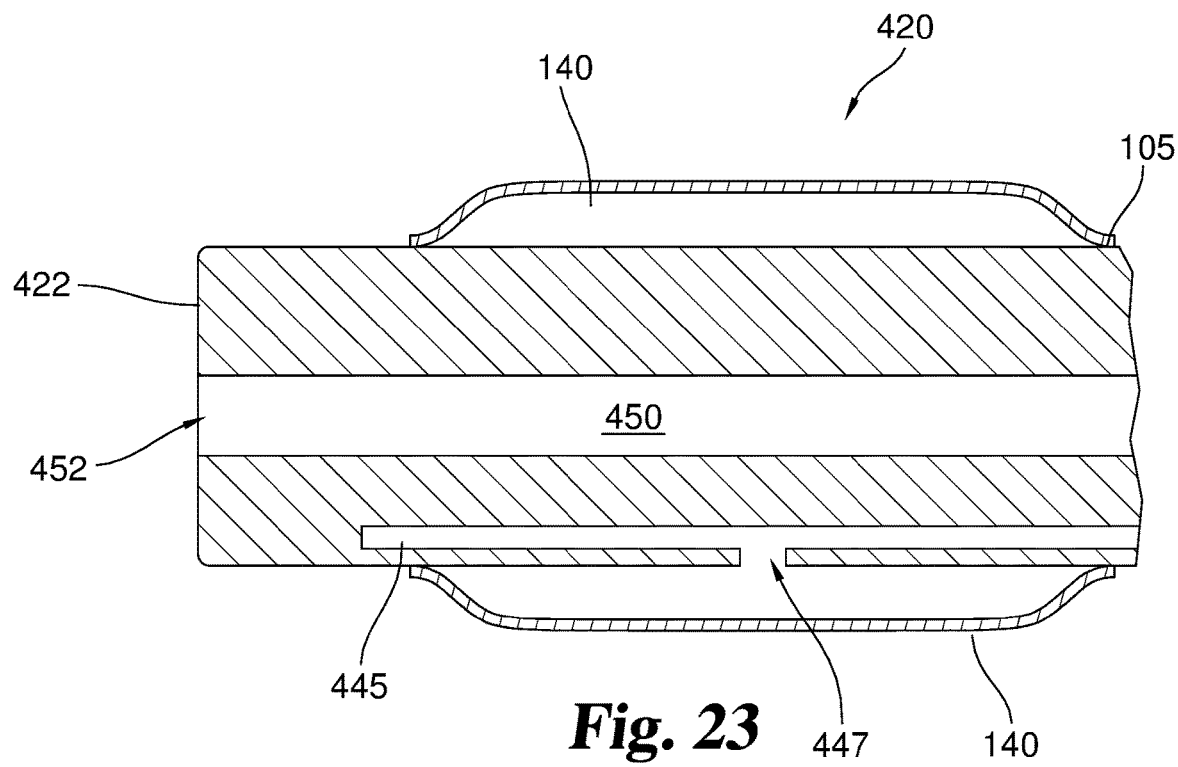
FIG. 23 is a cross-section view of an embodiment of a distal end of the catheter device of FIG. 11 with an injection lumen and a balloon inflation lumen.

FIG. 23 illustrates an embodiment of a distal end 420 of catheter device 100. Distal end 420 includes a distal tip 422, a balloon inflation lumen 445, and an injection lumen 450. Balloon inflation lumen 445 does not extend through the entire length of catheter 100 and is closed before reaching distal tip 422 of catheter 100. Injection lumen 450 extends through catheter 100, creating an injection lumen opening 452.

Injection lumen 450 is large enough for passage of a wire guide or a guide loop device, and may also allow passage of liquid and other material, such as biologic material, that is used for treatment. A guide wire or a guide loop device is inserted through injection lumen to aid in positioning catheter 100. Once distal end 420 is placed in the correct location, the guide wire or guide loop device is removed from catheter 100 to allow introduction of the treatment material through injection lumen 450 to the desired portion of the body.

Similar to the embodiment shown in FIG. 12, inflatable balloon 140 may be used to isolate a part of the body for treatment. Balloon inflation lumen 445 is in communication with inflation port 114 at the proximal end of catheter 100 and extends through catheter 100 to the distal end, at least to the position of inflatable balloon 140. An inflation passage 447 fluidly attaches balloon inflation lumen 445 to inflatable balloon 140. A fluid, for example air, may be introduced at inflation port 114, travel through inflation extension 113 and into balloon inflation lumen 445. The fluid then travels through balloon inflation lumen 445 to inflation passage 447 where it is introduced into inflatable balloon 140, causing inflatable balloon 140 to inflate.

Figure 24:
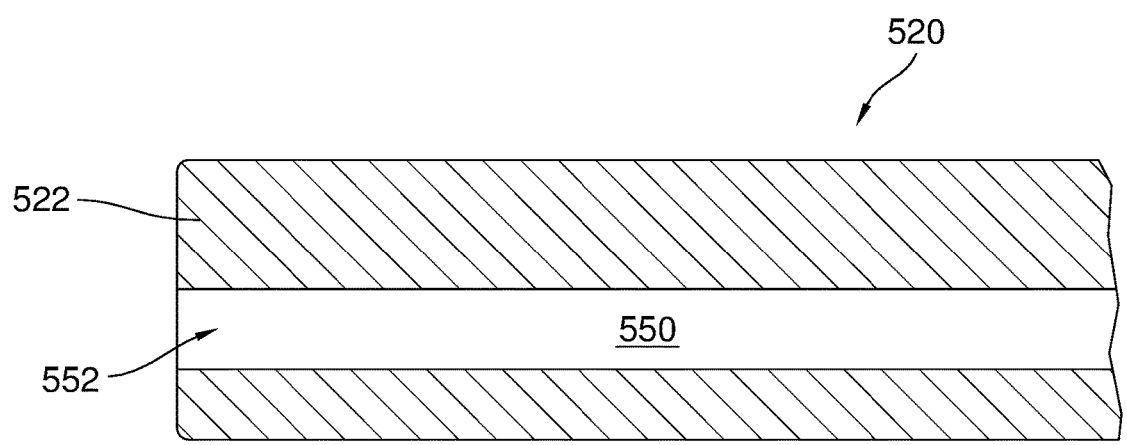
FIG. 24 is a cross-section view of an embodiment of a distal end of the catheter device of FIG. 11 with an injection lumen.

FIG. 24 shows an embodiment that includes distal end 520 of catheter 100 where catheter 100 is a single lumen catheter. Distal end 520 includes a distal tip 522 and an injection lumen 550 that extends through catheter 100. Injection lumen 550 is large enough for passage of a wire guide or a guide loop device, and may also allow passage of liquid or another flowable material, such as biologic material or therapeutic material, that is used for treatment. A guide wire or a guide loop device can be inserted through injection lumen to aid in positioning catheter 100. Once distal end 520 is placed in the correct location, the guide wire or guide loop device, if used, can be removed from catheter 100 to allow introduction of the treatment material through injection lumen 550 to the desired portion of the body.

Catheter 100 may be used to introduce a material, for example a biologic and/or therapeutic and/or diagnostic material, into the body. As an example, catheter 100 may be used to introduce such a material into the lungs. Catheter 100 is inserted into the airway passages of a patient. This may be accomplished by inserting catheter 100 through the neck and into a patient's trachea. Catheter 100 is moved into the patient's bronchi and through the patient's lungs until catheter 100 is positioned in a location adjacent to the portion of the lungs that requires treatment. Catheter 100 should be positioned so distal tip 222 does not contact the airway passage of the patient.

Positioning catheter 100 in the correct location can be accomplished by a variety of methods. If catheter 100 includes distal end 220, positioning of catheter 100 may be accomplished by standard wire guide placement methods or with the aid of a bronchoscope for visualizing the airway passages, where the wire guide is inserted into guide lumen 255. Alternatively, a guide loop device may be inserted through guide lumen 255 so the loop extends distally from distal tip 222. The loop is then attached to a bronchoscope which is used to guide catheter 100 to the correct location in the lungs.

If catheter 100 includes distal end 320, positioning catheter 100 may be accomplished by using tip deflecting wire 362. The operator may use a bronchoscope to view the position of catheter 100 in the lungs. Using the bronchoscope as a guide, the operator may deflect the tip deflecting wire 362 in the correct direction to move catheter 100 to the desired location in the lungs for treatment.

Figure 25:
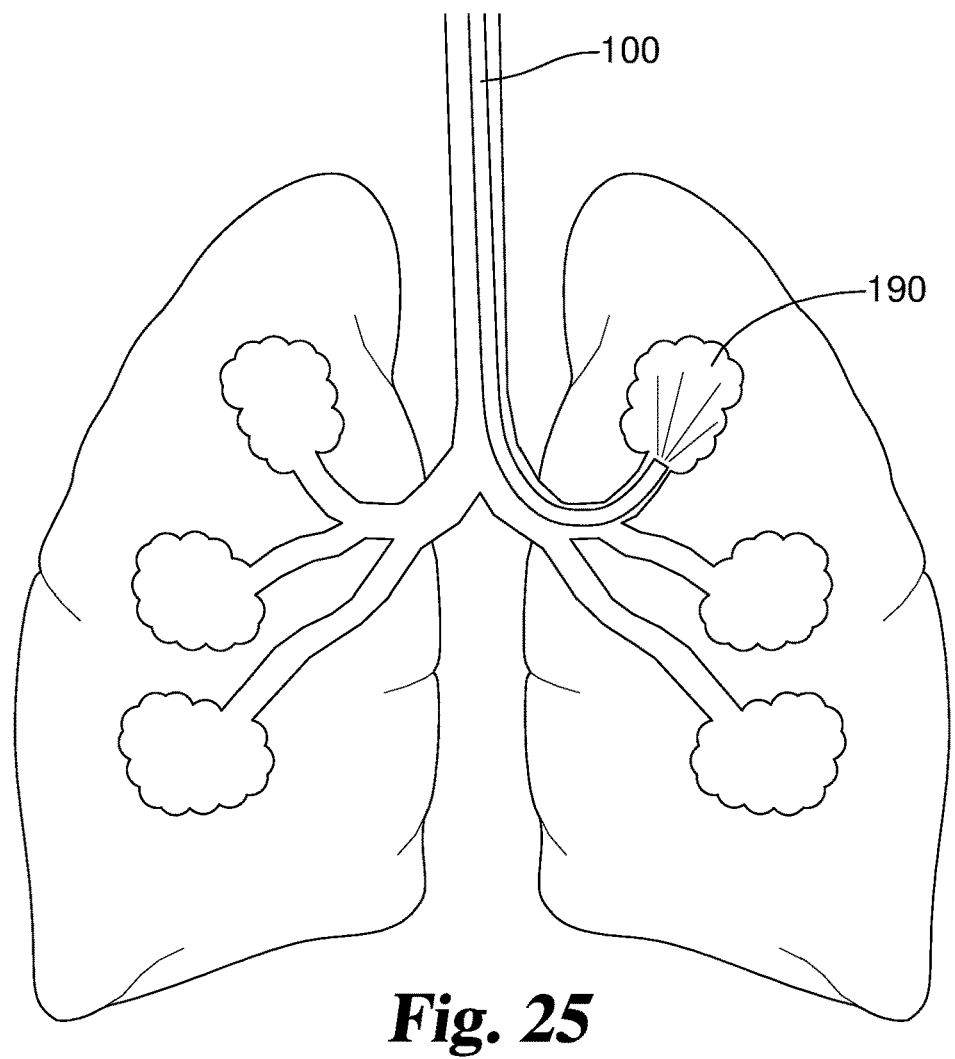
FIG. 25 is a view of the catheter device of FIG. 11 inserted into the airway passages of a patient.

Once catheter 100 is positioned near the portion of the airway passage 190 on which the biologic or other material is to be introduced, the operator may inflatable the inflatable balloon 140, such as a balloon, to isolate that portion of the airway passage. The balloon blocks airway passage 190 so that biologic or other material cannot move past the balloon and into the rest of the lungs (see FIG. 25).

Figure 26:
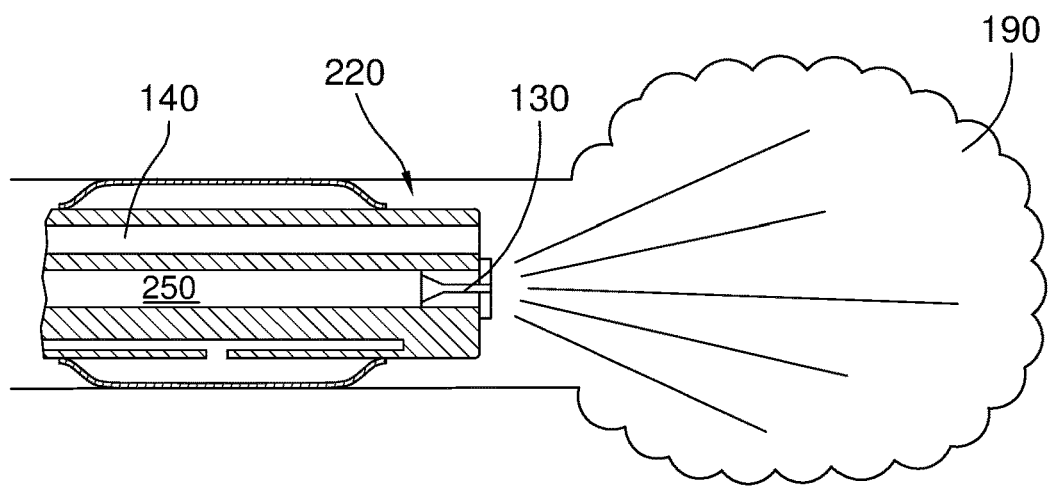
FIG. 26 is a view of the distal end of the catheter device of FIG. 19 inserted into the airway passages of a patient.

The biologic or other material is then passed into injection lumen 250. In some embodiments the biologic material may be passed into injection lumen by attaching a syringe to injection port 112. The attachment may be a luer lock or any other attachment method that secures the syringe to injection port 112. Flowable material from the syringe is passed into proximal hub 112 whereupon it passes into injection lumen 250. The material flows through injection lumen 250 to distal end 220 where it is passes through misting nozzle 130 and is sprayed onto the portion of the airway passages which need treatment (see e.g. FIG. 26).

With reference now to FIG. 27, shown is the distal region of another embodiment of a misting catheter 600. Catheter 600 includes an injection lumen 602 and a balloon inflation lumen 604. Balloon inflation lumen 604 fluidly communicates with inflation passage 606 which provides fluid communication between balloon inflation lumen 604 and the interior of balloon 608. Catheter 600 also includes a wire guide lumen 610 having an exit opening 612 positioned distal to balloon 608. Catheter 600 also includes a misting nozzle 614 having a stem 616.

Nozzle 614 is connected to the distal tip of catheter body 618 by a segment of coupler tubing 620 that receives therein both the stem 616 of the nozzle 614 and a distal most segment of the catheter body 618. Suitable bonding, such as adhesive bonding, can be used to secure the coupler tubing 620 to the stem 616 and catheter body 618 if needed or desired. It will be well understood that the proximal end of catheter 600 can be equipped with a hub or hubs providing inlet ports for each of the injection lumen 602, the balloon inflation lumen 604, and the wire guide lumen 610. These include for example manifold hubs as discussed herein.

With reference to FIG. 28, shown is the distal region of another embodiment of a misting catheter 600A. Catheter 600A includes components that are the same as catheter 600 discussed above in conjunction with FIG. 27, except the wire guide lumen 610A has an exit opening 612A positioned proximal to balloon 608. It will be understood that the proximal end of catheter 600A can be equipped with a hub or hubs providing inlet ports for each of the injection lumen 602, the balloon inflation lumen 604, and the wire guide lumen 610A. These include for example manifold hubs as discussed herein.

Figure 29:
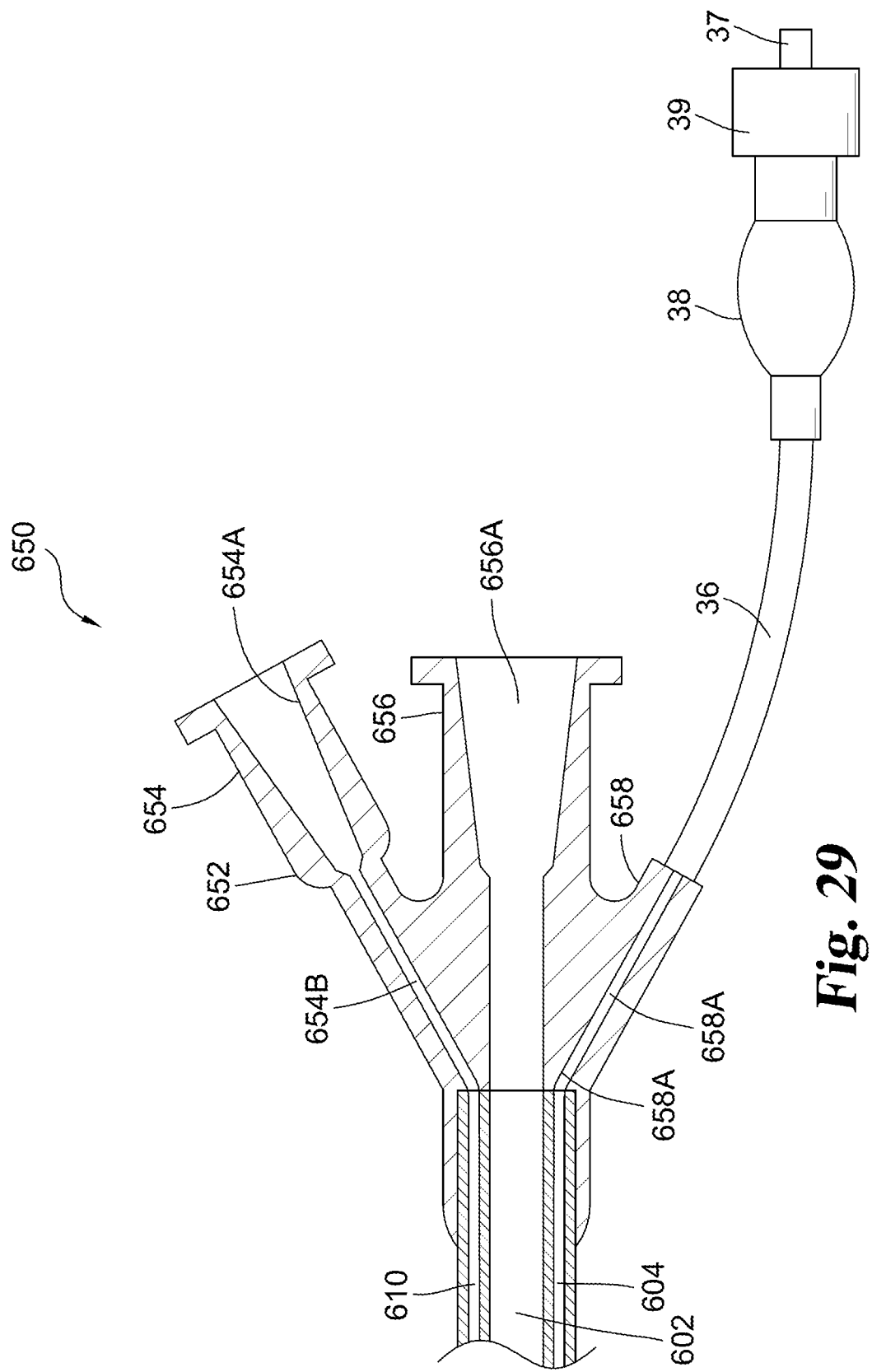
FIG. 29 provides an enlarged view, partially in cross section, of a proximal region of a catheter device.

Referring now to FIG. 29, shown is an embodiment of a proximal end of a misting catheter. Proximal end 650 includes a manifold hub 652 that defines a first extension member 654, a second extension member 656, and a third extension member 658. First extension member 654 defines a lumen therein having a first region 654A that has a decreasing lumen diameter as it extends distally and a second region 654B that has a constant or substantially constant diameter. Second extension member 656 defines a lumen having a first lumen region 656A that has a decreasing diameter as it extends distally and a second lumen region 656B that has a substantially constant or constant diameter. Third extension member 658 defines a lumen therein 658A having a substantially constant diameter. Manifold hub 652 is connected to a multilumen catheter body such as that discussed in conjunction with FIG. 27 or FIG. 28, as examples. As shown, the balloon inflation lumen 604 is in fluid communication with lumen 658A of third extension member 658, which in turn is equipped with an inflation tube and pilot balloon apparatus as discussed in conjunction with FIG. 1 above. It will be understood that proximal end 650 can also be used in conjunction with other multilumen misting catheters described herein that have an injection lumen, a wire guide lumen, and a balloon inflation lumen.

Figure 30:
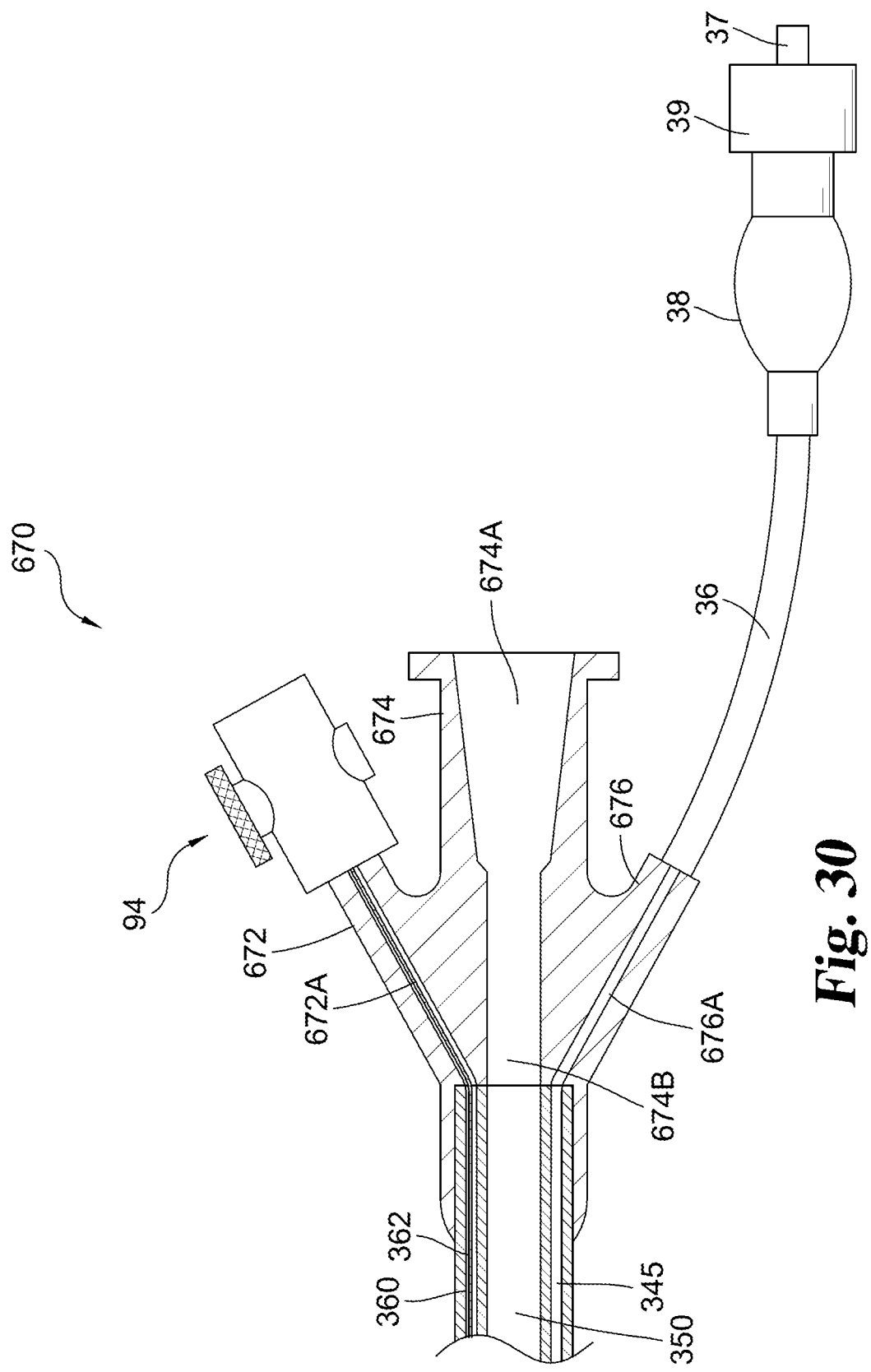
FIG. 30 provides an enlarged view, partially in cross section, of a proximal region of a catheter device with a tip deflecting wire and an independent fluid injection lumen.

Referring now to FIG. 30, shown is an embodiment of a proximal end 670 of a misting catheter. Proximal end 670 includes a manifold hub that defines a first extension member 672, a second extension member 674, and a third extension member 676. First extension member 672 defines a lumen 672A therein. Second extension member 674 defines a lumen having a first lumen region 674A that has a decreasing diameter as it extends distally and a second lumen region 674B that has a substantially constant or constant diameter. Third extension member 676 defines a lumen 676A therein. Manifold hub is connected to a multilumen catheter shaft, such as that discussed in conjunction with FIG. 27, for example. In particular, extension 672 has attached thereto a catheter deflection assembly 94 as discussed in conjunction with FIGS. 8-10 above, with the deflecting wire slidably received through lumen 672A.

Lumen 674A of extension member 674 provides an injection port, and extension member 676 is equipped with an inflation tube and pilot balloon apparatus as discussed in conjunction with FIG. 1 above, which fluidly communicate with lumen 676A. It will be understood that proximal end 670 can also be used in conjunction with other multilumen misting catheters described herein that have an injection lumen, a deflecting wire lumen, and a balloon inflation lumen.

Catheter devices and delivery assemblies including them as described herein can be used to deliver a flowable material to a bodily passage, such as a region within a lung, in a variety of ways. In certain forms, the bodily passage or region to be treated can be evacuated prior to delivery of the flowable material into the passage or region. For example, using catheters herein that include at least an injection lumen and an inflatable balloon, after inflation of the balloon to isolate the passage or region, a vacuum can be applied to the injection port fluidly communicating with the injection lumen to evacuate the passage or region, for example using a syringe or other device. In cases where the bodily passage is a region of a lung, this can cause a temporary contraction or collapse of the passage or region. After this evacuating, a syringe or other reservoir containing the flowable material to be introduced can be attached to the injection port, while maintaining all or at least a portion of the applied vacuum, and then the flowable material passed under pressure through the injection lumen for application to the isolated passage or region. Conventional means can be used to facilitate maintaining the applied vacuum while connecting the syringe/reservoir containing the flowable material to the injection port, including for example clamps or stopcocks. In other embodiments in which the catheter device includes both an injection lumen and a guide wire or other lumen both extending past the inflatable balloon and communicating with the isolated passage or region, the passage or region can be evacuated by applying a vacuum to the guide wire or other lumen while maintaining a seal or substantial seal of the injection lumen (e.g. using a clamp or stopcock or by pre-connecting the flowable material-filled syringe to the injection port). Thereafter, the guide wire or other lumen can be sealed to retain all or at least a portion of the applied vacuum, and the flowable material can then be introduced into the isolated and evacuated passage or region (e.g. as a mist as described herein). These and other modes of using the disclosed catheter devices and related delivery apparatuses will be apparent to those of ordinary skill in the field from the descriptions herein.

In addition to or as an alternative to the deflection-based steering mechanisms discussed above, catheters as disclosed herein can also be guided to a desired location within the lungs or another cavity of the body in other ways. For example, in some embodiments, magnetic guidance may be used as an alternative method of guiding catheter 90. In embodiments using magnetic guidance, a magnet can be embedded near the distal end of catheter 90. The magnet within catheter 90 interacts with a surrounding magnetic field that may be manipulated by an operator to facilitate guiding catheter 90 to a desired position or orientation within the body. In some embodiments, the operator may physically adjust or move the magnetic field. Alternatively, the magnet may be an electromagnet, and the magnetic field may be adjusted remotely by altering the current applied to the magnet.

Catheters and delivery apparatuses described herein can be used to deliver a variety of materials, including for example therapeutic or diagnostic substances, to bodily passageways of a patient. In preferred uses, the bodily passageway is an airway passage of a patient, such as an airway passage within a lung. Suitable therapeutic substances include biologic substances. Such biologic substances in certain embodiments include viable cells.

A wide variety of cell types may be used in embodiments of the present disclosure. For example, the cells can be skin cells, skeletal muscle cells, cardiac muscle cells, lung cells, mesentery cells, adipose cells, or stem cells such as mesenchymal stem cells. Adipose cells may be from omental fat, properitoneal fat, perirenal fat, pericardial fat, subcutaneous fat, breast fat, or epididymal fat. In certain embodiments, the cells comprise stromal cells, stem cells, or combinations thereof. As used herein, the term "stem cells" is used in a broad sense and includes traditional stem cells, adipose derived stem cells, progenitor cells, preprogenitor cells, reserve cells, and the like. Exemplary stem cells include embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Additional illustrative cells which can be used include hepatocytes, epithelial cells, Kupffer cells, fibroblasts, neurons, cardiomyocytes, myocytes, chondrocytes, pancreatic acinar cells, islets of Langerhans, osteocytes, myoblasts, satellite cells, endothelial cells, adipocytes, preadipocytes, biliary epithelial cells, and progentior cells of any of these cell types.

When used, mesenchymal stem cells (MSC) can be obtained from any suitable tissue. These include as examples MSCs derived from dental tissue (such as those harvested from dental pulp, periodontal ligaments, or other dental tissues), testicle tissue, bone marrow; peripheral blood, placental tissue, uterine tissue (including endometrial regenerative cells), umbilical cord blood, umbilical cord tissue, or skin tissue (including full thickness skin tissue). These or other MSCs can be used in aspects of the present disclosure. The MSCs can be generally an adherent cell population expressing markers CD90 and CD 105 (>90%) and lacking expression of CD34 and CD45 and MHC class II (<5%) as detected by flow cytometry.

The cells, when used in the embodiments herein, can be from any suitable species of animal, for example a mammal, such as a human, canine (e.g. dog), feline (e.g. cat), equine (e.g. horse), porcine, ovine, caprine, or bovine mammal.

A therapeutic substance used in embodiments herein can also be a biologic substance other than cells. These include for example biologic substances that are purified from biological tissue sources or biologic substances that are synthetically produced, for example using recombinant DNA technology.

In some forms the biologic substance will be a bioactive fraction of mammalian platelets, such as a platelet lysate composition. In certain embodiments the platelet lysate composition comprises a human platelet lysate (hPL) composition. The platelet lysate composition can contain multiple growth factors. These can include, for example, transforming growth factor beta 1 (TGF-β1), epidermal growth factor (EGF), basic fibroblast growth factor (FGF-b), platelet derived growth factor AA (PDGF-AA), platelet derived growth factor BB (PDGF-BB), stromal cell-derived factor-1 α (SDF-1α), and/or vascular endothelial growth factor (VEGF). The platelet lysate can also include one or more components derived from plasma in the platelet concentrate starting material, including for example fibrinogen, globulins, albumen, triglycerides, glucose, sodium, calcium, and/ or cholesterol. The platelet lysate can also contain other bioactive substances, for example one or more interleukins, interferons, and/or tumor necrosis factors. These interleukin(s), interferon(s) and/or tumor necrosis factor(s) may include, for example, one, some, or all of interleukin (IL)-1b, IL-6, IL-8, IL-10, IL-13, IL-17, interferon-gamma (IFN-gamma), and tumor necrosis factor-alpha (TNF-alpha).

In some forms the biologic substance will include a cell conditioned medium (a medium containing growth factors, cytokines and/or other biologically active substances secreted by cells that are cultured in the medium) or a fraction thereof. In certain embodiments, the cell conditioned medium will be a stem cell conditioned medium, such as a mesenchymal stem cell conditioned medium.

In still other embodiments, the therapeutic substance will include biologically active agents, such as drugs. A wide variety of biologically active agents may be used including for example antimicrobial agents such as penicillin, tetracycline, chloramphenicol, minocycline, doxycycline, vancomycin, bacitracin, kanamycin, neomycin, gentamycin, erythromycin and cephalosporins. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone, and antiseptics (substances that prevent or arrest the growth or action of microorganisms, generally in a nonspecific fashion) such as silver sulfadiazine, chlorhexidine, sodium hypochlorite, phenols, phenolic compounds, iodophor compounds, quaternary ammonium compounds, and chlorine compounds. Still other drugs can be anti-inflammatory agents, anti-proliferative agents, nonsteroidal anti-inflammatory drugs (NSAIDs), and others.

It will be understood that in beneficial embodiments, the catheter devices, apparatuses and/or methods described herein can be used to treat a lung or lungs of a human or other animal patient having a disease, disorder or injury of the lung or lungs, for example a human or other animal patient having Chronic Obstructive Pulmonary Disease (COPD). For these purposes cells and/or pharmaceutical agents can be delivered to interior passageways of the lungs as a mist or mists using the catheter devices, apparatuses or methods. It will also be understood that such catheter devices, apparatuses and/or methods may also be used to treat a disease, disorder or injury of tissue lining or accessible for mist deposit from other body passageways or cavities, for example tissue lining or accessible for mist deposit from within the abdominal passageway or cavity.

The use of the terms "a" and "an" and "the" and similar referents in the context of describing the embodiments especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

The invention claimed is:

1. A catheter device for introducing a material into a body cavity comprising:
    a catheter shaft having a proximal portion and a distal portion;
    a first lumen extending through the catheter shaft from the proximal portion to the distal portion;
    a second lumen extending through the catheter shaft from the proximal portion to the distal portion;
    a misting nozzle carried on the distal portion and fluidly coupled to the first lumen, the misting nozzle configured to receive a flow of liquid through the first lumen and form a mist of the liquid;
    a deflecting wire received in the second lumen, the deflecting wire having a distal portion attached to the distal portion of the catheter shaft and a proximal portion;
    an actuator coupled to the proximal portion of the deflecting wire and selectively operable to tension the deflecting wire to deflect the distal portion of the catheter shaft;
    an inflatable balloon mounted to the catheter shaft, wherein said inflatable balloon has an uninflated condition and an inflated condition;
    and
    wherein the first lumen and the second lumen are both in fluid communication with an interior of an actuator housing in which the proximal portion of the deflecting wire is received;
    wherein the distal portion of the catheter shaft is deflectable to selectively alter a throw direction of a mist formed by the catheter device while the inflatable balloon is in the inflated condition and sealed against an airway of a patient.

2. The device of claim 1, also comprising a third lumen extending through the catheter shaft, the third lumen fluidly communicating with an interior of the inflatable balloon and configured for passage of fluid to inflate the balloon.

3. The device of claim 2, wherein the device has a longitudinal profile, wherein the misting nozzle defines an outer profile within the longitudinal profile of the catheter device, wherein a distal end opening defines an outer profile within the longitudinal profile of the catheter device, and wherein the outer profile defined by the misting nozzle does not overlap the outer profile defined by the distal end opening.

4. The device of claim 1, wherein: the actuator comprises a spindle passing through at least a first opening of the actuator housing; the proximal portion of the deflecting wire is attached to the spindle; a first liquid-tight seal is provided between the first opening of the actuator housing and the spindle, the first liquid-tight seal allowing the rotation of the spindle in the first opening.

5. The device of claim 4, wherein:
the first liquid-tight seal remains liquid-tight to a liquid pressure of at least 1000 mmHg.

6. The device of claim 4, wherein the first liquid-tight seal comprises an elastomeric member compressed against an exterior surface of the actuator housing and against an exterior surface of the spindle.

7. The device of claim 6, wherein the elastomeric member is a gasket or O-ring.

8. The device of claim 4, wherein:
the actuator housing has a second opening;
the spindle also passes through the second opening; and
a second liquid-tight seal is provided between the second opening of the actuator housing and the spindle, the second liquid-tight seal allowing the rotation of the spindle in the second opening.

9. The device of claim 8, wherein:
the second liquid-tight seal remains liquid-tight to a liquid pressure of at least 1000 mmHg.

10. The device of claim 4, also comprising: an injection port in fluid communication with the first lumen and the interior of the actuator housing; wherein liquid passed into the injection port enters the interior of the actuator housing, contacts the spindle and proximal portion of the deflecting wire, and then passes through the first lumen.

11. A catheter device for introducing a material into a body cavity comprising:
a catheter shaft;
a first lumen extending through the catheter shaft;
a misting nozzle fluidly coupled to the first lumen and configured to provide a mist from a flow of liquid through the first lumen, the misting nozzle defining an outer profile within a longitudinal profile of the catheter device;
a second lumen extending through the catheter shaft;
a deflecting wire received in the second lumen, the deflecting wire having a distal portion attached to the distal portion of the catheter shaft and a proximal portion;
an actuator coupled to the proximal portion of the deflecting wire;
an inflatable balloon mounted to the catheter shaft proximal of the misting nozzle, wherein said inflatable balloon has an uninflated condition and an inflated condition;
and wherein the first lumen and the second lumen are both in fluid communication with an interior of an actuator housing in which the proximal portion of the deflecting wire is received;
wherein the deflecting wire is configured so that tensioning the tip of the deflecting wire deflects the distal portion of the catheter shaft;
and wherein the distal portion of the catheter shaft is deflectable to selectively alter a throw direction of a mist formed by the catheter device while the inflatable balloon is in the inflated condition and sealed against an airway of a patient.

12. The device of claim 11, wherein the catheter shaft has an outer profile within the longitudinal profile of the catheter device, and wherein the outer profile of the misting nozzle is within the outer profile of the catheter shaft.

13. The device of claim 11, wherein:
the actuator comprises a spindle passing through at least a first opening of the actuator housing;
the proximal portion of the wire is attached to the spindle;
a first liquid-tight seal is provided between the first opening of the actuator housing and the spindle, the first liquid-tight seal allowing the rotation of the spindle in the first opening.

14. The device of claim 13, wherein:
the first liquid-tight seal remains liquid-tight to a liquid pressure of at least 1000 mmHg.

15. The device of claim 13, wherein the first liquid-tight seal comprises an elastomeric member compressed against an exterior surface of the actuator housing and against an exterior surface of the spindle.

16. The device of claim 13, wherein:
the actuator housing has a second opening;
the spindle also passes through the second opening; and
a second liquid-tight seal is provided between the second opening of the actuator housing and the spindle, the second liquid-tight seal allowing the rotation of the spindle in the second opening.

17. The device of claim 16, wherein:
the second liquid-tight seal remains liquid-tight to a liquid pressure of at least 1000 mmHg.

18. The device of claim 13, also comprising: an injection port in fluid communication with the first lumen and the interior of the actuator housing; wherein liquid passed into the injection port enters the interior of the actuator housing, contacts the spindle and proximal portion of the deflecting wire, and then passes through the first lumen.

* * * * *